(12) United States Patent
Gharieb et al.

(10) Patent No.: US 8,190,249 B1
(45) Date of Patent: May 29, 2012

(54) MULTI-PARAMETRIC QUANTITATIVE ANALYSIS OF BIOELECTRICAL SIGNALS

(75) Inventors: Reda R. Gharieb, Baltimore, MD (US); Manan Hathi, Cockeysville, MD (US); Santosh Venkatasha, Baltimore, MD (US); David Sherman, Parkville, MD (US); Neil Rothman, Baltimore, MD (US); Margaret Natarajan, San Marino, CA (US); Ananth Naturajan, San Marino, CA (US)

(73) Assignee: Infinite Biomedical Technologies, LLC, Baltimore, MD (US)

( * ) Notice: Subject to any disclaimer, the term of this patent is extended or adjusted under 35 U.S.C. 154(b) by 1536 days.

(21) Appl. No.: 11/496,925

(22) Filed: Aug. 1, 2006
(Under 37 CFR 1.47)

Related U.S. Application Data

(60) Provisional application No. 60/704,326, filed on Aug. 1, 2005.

(51) Int. Cl.
*A61B 5/04* (2006.01)
(52) U.S. Cl. .................. 600/544; 600/545; 600/508
(58) Field of Classification Search .................. 600/544, 600/545
See application file for complete search history.

(56) References Cited

U.S. PATENT DOCUMENTS

| | | | | |
|---|---|---|---|---|
| 4,201,224 A | * | 5/1980 | John | 600/544 |
| 5,083,571 A | * | 1/1992 | Prichep | 600/544 |
| 5,458,117 A | * | 10/1995 | Chamoun et al. | 600/547 |
| 5,724,987 A | * | 3/1998 | Gevins et al. | 600/544 |

OTHER PUBLICATIONS

Amir, N. and I. Gath, "Segmentation of EEG During Sleep Using Time-Varying Autoregressive Modeling", Biological Cybernetics, 61, 1989, 9 pp.
Amodio, P., P. Marchetti, F. Del Piccolo, M. De Tourtchaninoff, P. Varghese, C. Zuliani, G. Campo, A. Gatta, and J. M. Guerit, "Spectral Versus Visual EEG Analysis in Mild Hepatic Encephalopathy", Clinical Neurophysiology, 110 (8), 1999, 11 pp.
Anderson, C.W., E.A. Stolz, and S. Shamsunder, "Multivariate Autoregressive Models for Classification of Spontaneous Electroencephalographic Signals During Mental Tasks," IEEE Transactions on Biomedical Engineering, vol. 45, No. 3, Mar. 1998, 10 pp.
Azzopardi, D., I. Guarino, C. Brayshaw, F. Cowan, D. Price-Williams, A.D. Edwards, and D. Acolet, "Prediction of Neurological Outcome After Birth Asphyxia From Early Continuous Two-Channel Electroencephalography", Early Human Development, 55(2), 1999, 11 pp.
Bassetti, C., F. Bomio, J. Mathis, and C.W. Hess, "Early Prognosis in Coma After Cardiac Arrest: A Prospective Clinical, Electrophysiological, and Biochemical Study of 60 Patients", Journal of Neurology, Neurosurgery, and Psychiatry, 61(6), 1996, 7 pp.

(Continued)

*Primary Examiner* — Patricia Mallari
(74) *Attorney, Agent, or Firm* — Konrad Raynes & Victor LLP; Alan S. Raynes

(57) ABSTRACT

Certain embodiments relate to a method for determining a condition of a subject, including obtaining a signal, the signal including a plurality of determinable parameters. The method also includes determining at least two of the plurality of determinable parameters from the signal, to yield determined parameters. The method also includes applying a weighting factor to each of the determined parameters to yield weighted parameters, and combining the weighted parameters to determine a numeric value relating to the condition of the subject. Other embodiments are described and claimed.

35 Claims, 23 Drawing Sheets

OTHER PUBLICATIONS

Berkhoff, M., F. Donati, and C. Bassetti, "Postanoxic Alpha (Theta) Coma: A Reappraisal of Its Prognositc Significance", Clinical Neurophysiology, 111 (2), 2000, 8 pp.

Bezerianos, A., S. Tong, and N. Thakor, "Time-Dependent Entropy Estimation of EEG Rhythm Changes Following Brain Ischemia," Annals of Biomedical Engineering, vol. 31, 2003, 12 pp.

Booth, C.M., R.H. Boone, G. Tomlinson, and A.S. Detsky, "Is This Patient Dead, Vegetative, or Severely Neurologically Impaired? Assessing Outcome for Comatose Survivors of Cardiac Arrest", Journal of the American Medical Association, vol. 291, No. 7, Feb. 18, 2004, 10 pp.

Cummins, R.O., D. Chamberlain, M.F. Hazinski, V. Nadkarni, W. Kloeck, E. Kramer, L. Becker, C. Robertson, R. Koster, A. Zaritsky, L. Bossaert, J.P. Ornato, V. Callanan, M. Allen, P. Steen, B. Connolly, A. Sanders, A. Idris, and S. Cobbe, "Recommended Guidelines for Reviewing, Reporting, and Conducting Research on In-Hospital Resuscitation: The In-Hospital "Utstein style"", Annals of Emergency Medicine, 29 (5), May 1997, 30 pp.

Edgren, E., U. Hedstrand, S. Kelsey, K. Sutton-Tyrrell, P. Safar, and Brct I Study Group, "Assessment of Neurological Prognosis in Comatose Survivors of Cardiac Arrest", The Lancet, vol. 343, Apr. 30, 1994, 5 pp.

Edgren, E., U. Hedstrand, M. Nordin, E. Rydin, and G. Ronquist, "Prediction of Outcome After Cardiac Arrest", Critical Care Medicine, vol. 15, No. 9, © 1987, 6 pp.

Florence, G., J. Guerit, and B. Gueguen, "Electroencephalography (EEG) and Somatosensory Evoked Potentials (SEP) to Prevent Cerebral Ischaemia in the Operating Room", Clinical Neurophysiology, 34 (1), 2004, 16 pp.

Geocadin, R.G., R. Ghodadra, T. Kimura, H. Lei, D.L. Sherman, D.F. Hanley, and N.V. Thakor, "A Novel Quantitative EEG Injury Measure of Global Cerebral Ischemia", Clinical Neurophysiology, 111, 2000, 9 pp.

Geocadin, R.G., D.L. Sherman, H.C. Hansen, T. Kimura, E. Niedermeyer, N.V. Thakor, and D.F. Hanley, "Neurological Recovery by EEG Bursting After Resuscitation from Cardiac Arrest in Rats", Resuscitation, 55, 2002, 8 pp.

Gharieb, R.R. and A. Cichocki, "Segmentation and Tracking of EEG Signal Using an Adaptive Recursive Bandpass Filter," Medical and Biological Engineering and Computing, vol. 39, Jan. 2001, 12 pp.

Goto, S., M. Nakamura, and K. Uosaki, "On-Line Spectral Estimation of Non-Stationary Time Series Based on AR Model Parameter Estimation and Order Selection with a Forgetting Factor", IEEE Transactions on Signal Processing, vol. 43, No. 6, Jun. 1995, 4 pp.

Guerit, J.M., "Medical Technology Assessment EEG and Evoked Potentials in the Intensive Care Unit", Clinical Neurophysiology, vol. 29, No. 4, 1999, 17 pp.

Gutling, E., S. Isenmann, and W. Wichmann, "Electrophysiology in the Locked-In-Syndrome", Neurology, 46(4), 1996, 10 pp.

Hovland, A., E.W. Nielsen, J. Kluver and R. Salvesen, "EEG Should be Performed During Induced Hypothermia", Resuscitation, 68(1), 2006, 4 pp.

Husain, A.M., "Electroencephalographic Assessment of Coma", Journal of Clinical Neurophysiology, vol. 23, No. 3, Jun. 2006, 13 pp.

Jorgensen E.O. and A. Malchow-Moller, "Natural History of Global and Critical Brain Ischaemia", Part I: EEG and Neurological Signs During the First Year After Cardiopulmonary Resuscitation in Patients Subsequently Regaining Consciousness, Resuscitation, 9, 1981, 21 pp.

Jorgensen E.O. and A. Malchow-Moller, "Natural History of Global and Critical Brain Ischaemia", Part II: EEG and Neurological in Patients Remaining Unconscious After Cardiopulmonary Resuscitation, Resuscitation, 9, 1981, 20 pp.

Kaplan, P.W., "Electrophysiological Prognostication and Brain Injury from Cardiac Arrest", Seminars in Neurology, 26, 2006, 10 pp.

Kaplan, P.W., D Genoud, T.W. Ho, and P. Jallon, "Clinical Correlates and Prognosis in Early Spindle Coma", Clinical Neurophysiology, 111(4), 2000, 7 pp.

Kaplan, P.W., D. Genoud, T.W. Ho, and P. Jallon, "Etiology, Neurologic Correlations, and Prognosis in Alpha Coma", Clinical Neurophysiology, 110(2), 1999, 9 pp.

Koenig, M.A., P.W. Kaplan, and N.V. Thakor, "Clinical Neurophysiologic Monitoring and Brain Injury From Cardiac Arrest", Neurologic Clincs, 24(1), 2006, 18 pp.

Kong, X., A. Brambrink, D.F. Hanley, and N.V. Thakor, "Quantification of Injury-Related EEG Signal Changes Using Distance Measures", IEEE Transactions on Biomedical Engineering, vol. 46, No. 7, Jul. 1999, 3 pp.

Lopes Da Silva, F., "EEG Analysis: Theory and Practice", Electroencephalography: Basic Principles, Clinical Applications, and Related Fields, Fourth Edition, Eds. E. Niedermeyer & F. Lopes Da Silva, 1999, 31 pp.

Luft, A.R., M.M. Buitrago, J.S. Paul, J. Hagan, M. Ding, N. Thakor, and D.F. Hanley, "Early Restitution of Electrocorticogram Predicts Subsequent Behavioral Recovery from Cardiac Arrest", Journal of Clinical Neurophysiology, 19(6), 2002, 7 pp.

Pincus, S.M., "Approximate Entropy as a Measure of System Complexity", Proceedings of the National Academy of Sciences, USA, vol. 88, Mar. 1991, 5 pp.

Rundgren, M., I. Rosen, and H. Friberg, "Amplitude-Integrated EEG (aEEG) Predicts Outcome After Cardiac Arrest and Induced Hypothermia", Intensive Care Med, 32(6), 2006, 7 pp.

Sherman, D.L., A.M. Brambrink, R.N. Ichord, V.K. Dasika, R.C. Koehler, R.J. Traystman, D.F. Hanley, and N.V. Thakor, "Quantitative EEG During Early Recovery From Hypoxic-Ischemic Injury in Immature Piglets: Burst Occurrence and Duration", Clinical Electroencephalography, vol. 30, No. 4, 1999, 9 pp.

Sterz, F., A. Zeiner, I. Kurkciyan, K. Janata, M. Mullner, H. Domanovits, and P. Safar, "Mild Resuscitative Hypothermia and Outcome After Cardiopulmonary Resuscitation", Journal of Neurosurgical Anesthesiology, vol. 8, No. 1, 1996, 9 pp.

Synek, V.M., "Prognostically Important EEG Coma Patterns in Diffuse Anoxic and Traumatic Encephalopathies in Adults", Journal of Clinical Neurophysiology, 5(2), 1988, 14 pp.

Tharp, B.R., F. Cukuer, and N. Monod, "The Prognostic Value of the Electroencephalogram in Premature Infants", Electroencephalography and Clinical Neurophysiology, 51(3), 1981, 18 pp.

Tong, S., A. Bezerianos, A. Malhotra, Y. Zhu, and N. Thakor, "Parameterized Entropy Analysis of EEG Following Hypoxic-Ischemic Brain Injury", Physics Letters A, 314, 2003, 8 pp.

Tononi, G., O. Sporns, and G.M. Edelman, "A Complexity Measure for Selective Matching of Signals by the Brain", Proceedings of the National Academy of Sciences, USA, vol. 93, 1994, 6 pp.

Vakkuri, A., A. Yli-Hankala, P. Talja, S. Mustola, H. Tolvanen-Laakso, T. Sampson, and H. Viertio-Oja, "Time-Frequency Balanced Spectral Entropy as a Measure of Anesthetic Drug Effect in Central Nervous System During Sevoflurane, Propofol, and Thiopental Anesthesia", Acta Anaesthesiologica Scandinavica, 48, 2004, 9 pp.

Viertio-Oja, H., V. Maja, M. Sarkela, P. Talja, N. Tenkanen, H. Tolvanen-Laakso, M. Paloheimo, A. Vakkuri, A. Yli-Hankala, and P. Merilainen, "Description of Entropy Algorithm as Applied in the Datex-Ohmeda S/5TM Entropy Module", Acta Anaesthesiologica Scandinavica, vol. 48, 2004, 8 pp.

Wijdicks, E.F.M., A. Hijdra, G.B. Young, C.L. Bassetti, and S. Wiebe, "Practice Parameter: Prediction of Outcome in Comatose Survivors After Cardiopulmonary Resuscitation (An Evidence-Based Review): Report of the Quality Standards Subcommittee of the American Academy of Neurology", Neurology, 67(2), 2006, 8 pp.

Wright, J.J., R.R. Kydd, and A.A. Sergejew, "Autoregression Models of EEG", Biological Cybernetics, 62, 1990, 10 pp.

Yamashita, S., T. Morinaga, S. Ohgo, T. Sakamoto, N. Kaku, S. Sugimoto, and S. Matsukura, "Prognostic Value of Electroencephalogram (EEG) in Anoxic Encephalopathy After Cardiopulmonary Resuscitation: Relationship Among Anoxic Period, EEG Grading and Outcome", Internal Medicine, vol. 34, No. 2, Feb. 1995, 6 pp.

Young, G.B., W.T. Blume, V.M. Campbell, J.D. Demelo, L.S. Leung, M.J. Mckeown, R.S. Mclachlan, S.A. Ramsay, and J.R. Schieven, "Alpha, Theta and Alpha-Theta Coma: A Clinical Outcome Study Utilizing Serial Recordings", Electroencephalography and Clinical Neurophysiology, 91(2), 1994, 7 pp.

Young G.B., G. Doig, and A. Ragazzoni, "Anoxic-Ischemic Encephalopathy: Clinical and Electrophysiological Associations With Outcome", Neurocritical Care, 2(2), 2005, 6 pp.

Zandbergen, E.G.J., R.J. De Haan, J.H.T.M. Koelman, and A. Hijdra, "Prediction of Poor Outcome in Anoxic-Ischemic Coma", Journal of Clinical Neurophysiology, 17(5), 2000, 4 pp.

Zaret, B.S., "Prognostic and Neurophysiological Implications of Concurrent Burst Suppression and Alpha Patterns in the EEG of Post-Anoxic Coma", Electroencephalography and Clinical Neurophysiology, 61(4), 1985, 11 pp.

Ziv, J., and A. Lempel, "Compression of Individual Sequences via Variable-Rate Coding", IEEE Transactions on Information Theory, vol. IT-24, No. 5, Sep. 1978, 7 pp.

Abramson, N.S., P. Safar, K.M. Detre, S.F. Kelsey, J. Monroe, O. Reinmuth, and J.V. Snyder, "Neurologic Recovery After Cardiac Arrest: Effect of Duration of Ischemia", Critical Care Medicine, vol. 13, No. 11, 1985, 2 pp.

Cummins, R.O., D.A. Chamberlain, N.S. Abramson, M. Allen, P. Baskett, L. Becker, L. Bossaert, H. Delooz, W. Dick, M. Eisenberg, T. Evans, S. Holmberg, R. Kerber, A. Mullie, J.P. Ornato, E. Sandoe, A. Skulberg, H. Tunstall-Pedoe, R. Swanson, and W.H. Theis, "Recommended Guidelines for Uniform Reporting of Data From Out-of-Hospital Cardiac Arrest: The Utstein Style", Annals of Emergency Medicine, 20 (8), Aug. 1991, 14 pp.

Levy, D.E., J.J Caronna, B.H. Singer, R.H. Lapinski, H. Frydman, and F. Plum, "Predicting Outcome From Hypoxic-Ischemic Coma", Journal of the American Medical Association, Vol. 253, No. 10, Mar. 8, 1985, 7 pp.

Longstreth Jr., W.T., T.S. Inui, L.A. Cobb, and M.K. Copass, "Neurologic Recovery After Out-of-Hospital Cardiac Arrest", Annals of Internal Medicine, 98 (Part 1), 1983, 6 pp.

Vaagenes, P., M. Ginsberg, U. Ebmeyer, L. Ernster, M. Fischer, S. Gisvold, A. Gurvitch, K.A. Hossmann, E.M. Nemoto, A. Radovsky, J.W. Severinghaus, P. Safar, R. Schlichtig, F. Sterz, T. Tonnessen, R.J. White, X. Peng, and Y. Zhou, "Cerebral Resuscitation From Cardiac Arrest: Pathophysiologic Mechanisms", Critical Care Medicine, vol. 24(2S) Supplement, Feb. 1996, 26 pp.

\* cited by examiner

MULTI-PARAMETRIC QUANTITATIVE ANALYSIS OF BIOELECTRICAL SIGNALS

This application claims priority in U.S. Provisional Application No. 60/704,326, filed on Aug. 1, 2005, entitled "Method for EEG Quantitative Analysis and Monitoring," which is hereby incorporated by reference in its entirety.

This invention was made with government support under Grant Nos. HD042872 and HL070129 awarded by NIH (National Institutes of Health). The government has certain rights in the invention.

RELATED ART

A number of devices and methods are to some degree capable of tracking and analyzing bioelectrical activity. Despite the fact that considerable time and effort have been devoted by many researchers for analysis of bioelectrical signals, satisfactory extraction of the considerable amount of information in the signal is still not realized.

BRIEF DESCRIPTION OF THE DRAWINGS

Certain embodiments of the invention are described with reference to the accompanying drawings, which, for illustrative purposes, are not necessarily drawn to scale.

DETAILED DESCRIPTION

Figure 1:
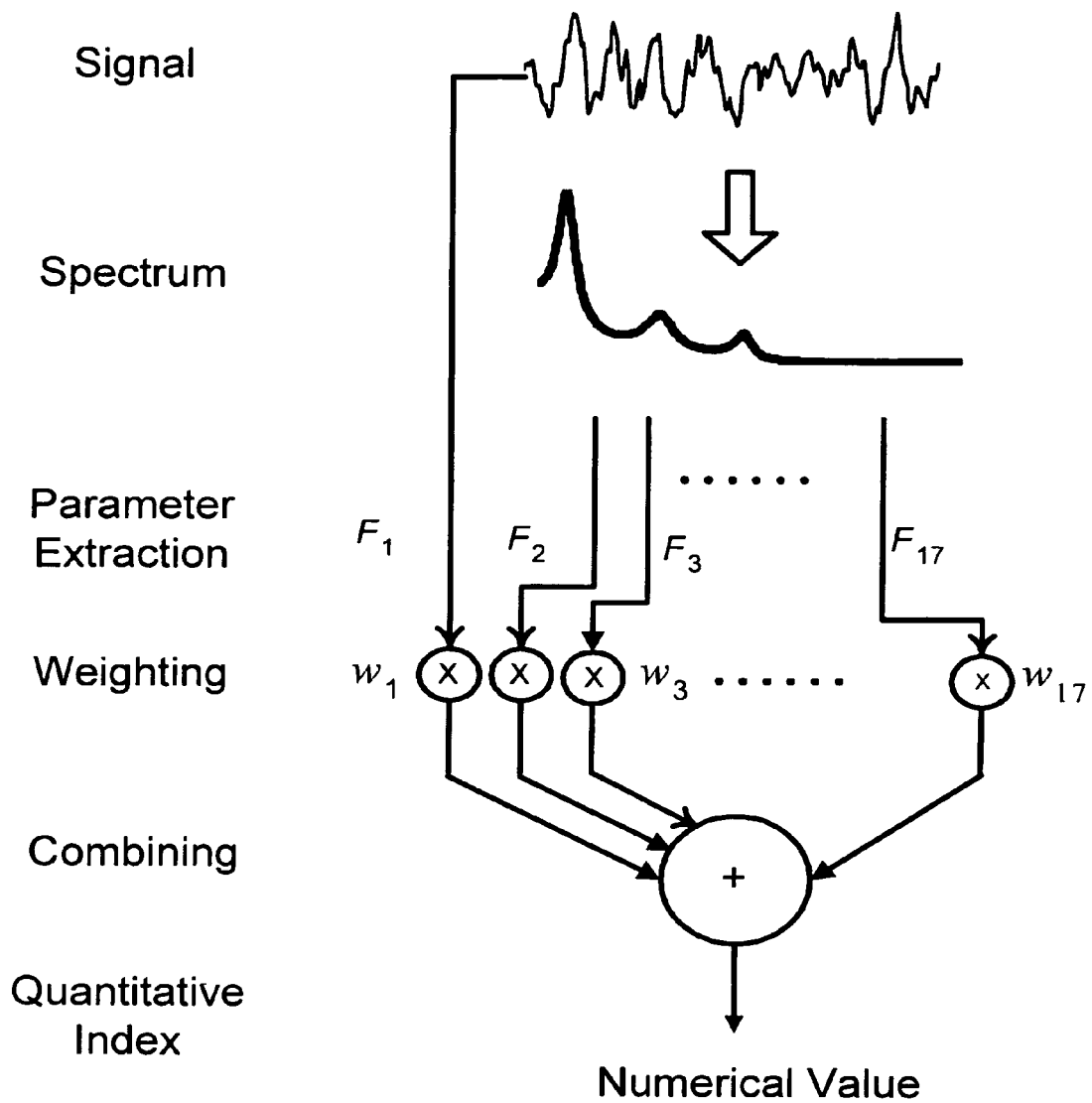
FIG. 1. illustrates an overall schematic of combining parameters of a bioelectrical signal to construct a quantitative index, in accordance with certain embodiments.

Visual interpretation of analog bioelectrical signals is generally restricted to analysis in the time domain and requires considerable training. The use of frequency and power spectrum analysis introduced basic signal processing of bioelectrical signals beyond visual inspection. Certain techniques based on frequency and power spectrum analysis have been employed for assessment of depth of anesthesia and for cerebral ischemia. Since the bioelectrical signals are typically the results of discharges from thousands of bioelectrically active cells, many prior approaches have treated bioelectrical signal as a wide frequency spectrum that is rich in harmonics and extremely complex (nonlinear) dynamics. Various spectral based methods have been employed for detection of cerebral activity changes. These methods don't use amplitude information and none of them uses all the information that can be extracted from the power spectral density. This limits these methods from application to a wide variety of brain dysfunctions.

Indices for assessment of EEG complexity involving amplitude-based entropy, approximate entropy, LZ complexity, the correlation dimension, embedding-subspace decomposition and wavelet entropy have been applied. The drawback of these indices arises from the fact that they don't use the frequency information of the EEG power spectrum. Spectral entropy has been used as a marker in quantitative EEG analysis and monitoring. This technique employs the Fast Fourier Transform (FFT) for computing the power spectrum of the EEG signal. The drawback of the FFT, and therefore techniques based on FFT, is due to its frequency resolution since it is the reciprocal of the data size. In one implementation, this approach computes the entropy of a predetermined frequency band and ignores the rest of the spectrum, reducing its sensitivity. In another approach, the entropy of the overall spectral band is computed, blunting the details of the entropy. Moreover, the technique doesn't use the information which can be extracted from the instantaneous EEG amplitude.

Therefore, a multi-parametric approach using the full range of applicable spectral, temporal, and probabilistic parameters to generate a quantitative index in the form of a numerical value may offer a unique capability to evaluate status of the relevant organ systems. There is a great need for quantitative analysis of bioelectrical signals that results in an accurate, sensitive, reliable and clinically relevant comprehensive numerical index. A device utilizing or displaying such an index could be of significant value to improving medical care.

The inventors have noted that two power spectral patterns having the same average power and same equivalent bandwidth can be distinguished based on how the power is distributed in relationship to both time and frequency. These power-frequency distribution characteristics can be measured by spectral complexity, which integrates power spectrum and complexity analysis. In an example, a single-tone signal is highly predictable and has a single line normalized power spectrum of unity value. Such a single-tone signal has a spectral complexity of zero. A signal in which sequential values are independent and identically distributed (i.e., a random signal) has uniformly distributed power spectral density. Hence, such a random signal has the maximum spectral complexity. The spectral complexity is then a measure of unpredictability or randomness characteristics and information contents of a signal as well. Bioelectrical signals may vary from single-tone like complexity to noise-like (maximum) complexity.

Additional information can be obtained by dividing the signal's overall spectrum into sub-bands and rhythms and computing the spectral complexity and power of each rhythm. The sub-band spectral complexity can then distinguish two signals having the same overall spectral complexity but different sub-band spectral complexities. Sub-band spectral complexities are band-variant which increases the sensitivity of the method. This makes the sub-band power and spectral complexity more likely to show quantitative differences between various bioelectrical signals and thus their corresponding underlying mechanisms.

Therefore, a multi-parametric approach that includes a range of spectral, temporal, and probabilistic parameters from the bioelectrical signal may offer a unique capability for evaluation of the status of the corresponding organ system. The specific parameter set selected can be used to empirically train an algorithm to provide a quantification of status using a relevant scale or scoring system. For maximum effectiveness, each specific parameter in the multi-parametric parameter set may be specifically selected to correspond to a spectral or temporal change in the signal corresponding to the specific clinical condition. Thus, though a single specific parameter may not be very effective in quantification, a multi-parametric approach draws on the strengths of each individual specific parameter and combines them into a value which reflects the status of the relevant organ system.

This multi-parametric approach of digital signal processing may be applied to quantitative analysis of both single and multiple channel signals. Such an approach may include a real-time, quantitative index for assessment and monitoring of the organ systems whose signals are being collected and analyzed. Some embodiments may use this index for making computer-based diagnosis, monitoring real-time change in the status of a subject, assessing response to treatment, predicting future outcome, and operating a brain-controlled computer or device in the manner of brain-computer interface.

This quantitative index may be utilized to determine the status of the subject. Such a method can be realized as a linear, nonlinear, or neural network system. A quantitative index is obtained as the output of a pre-trained system using a relevant set of signal parameters for a particular clinical condition. FIG. 1 illustrates the overall process of constructing a quantitative index from a bioelectrical signal, in accordance with certain embodiments. An EEG waveform is shown as an example. In this embodiment, changes in neuronal status results in changes in the spectrum of the EEG signal. These changes are captured by extracting a combination of multiple specific parameters ($F_i$). Appropriate weighting factors ($w_i$) for the specific parameters are then determined and applied. The weighted parameters are then combined, yielding a quantitative index which reflects the status of the brain.

A detailed description of a method for determining the quantitative index in accordance with certain embodiments will be discussed below. This method, in accordance with certain embodiments, starts by collecting a signal and passing it through an analog-to-digital converter (ADC) with an appropriate sampling frequency. To enhance the EEG signal, a bandpass filter may be employed. Windowing is then performed by dividing the enhanced signal into windows of a predetermined duration for further analysis. Artifact-ridden data windows are rejected. A combination of the most significant parameters is then employed.

Figure 6:
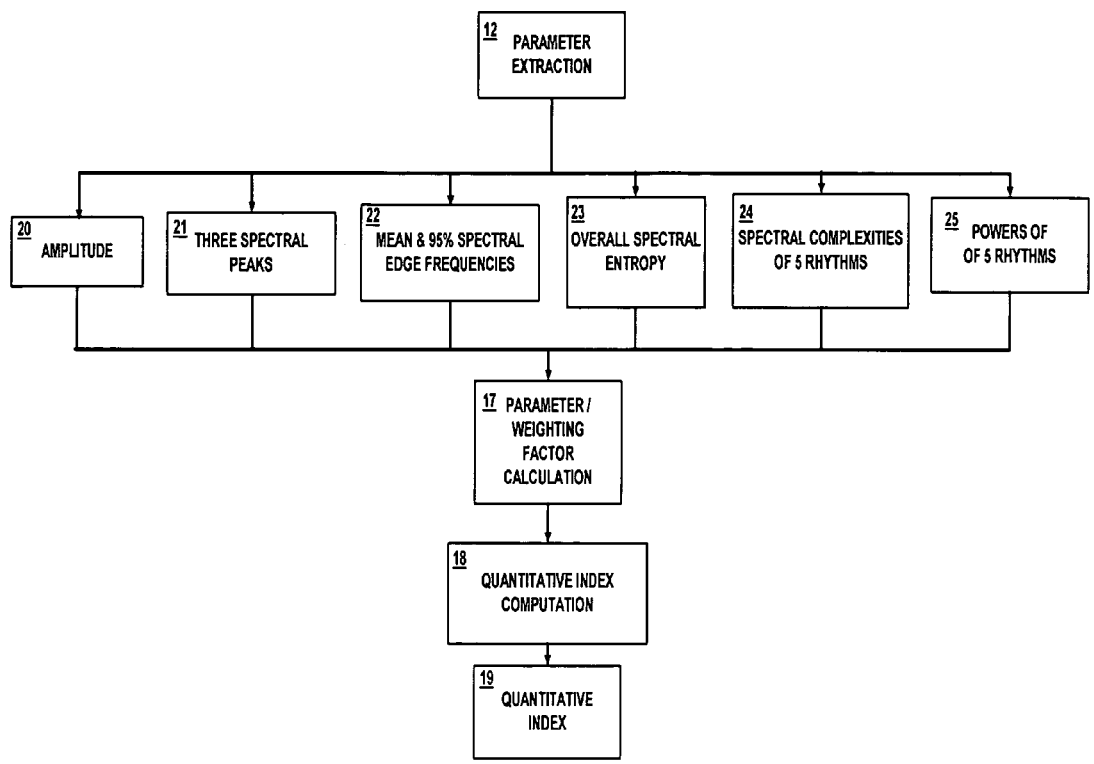
FIG. 6 specifies a set of EEG parameters chosen for neuronal injury detection and illustrates a schematic of combining the parameters to construct a quantitative index for neuronal injury detection, in accordance with certain embodiments.
Figure 7:
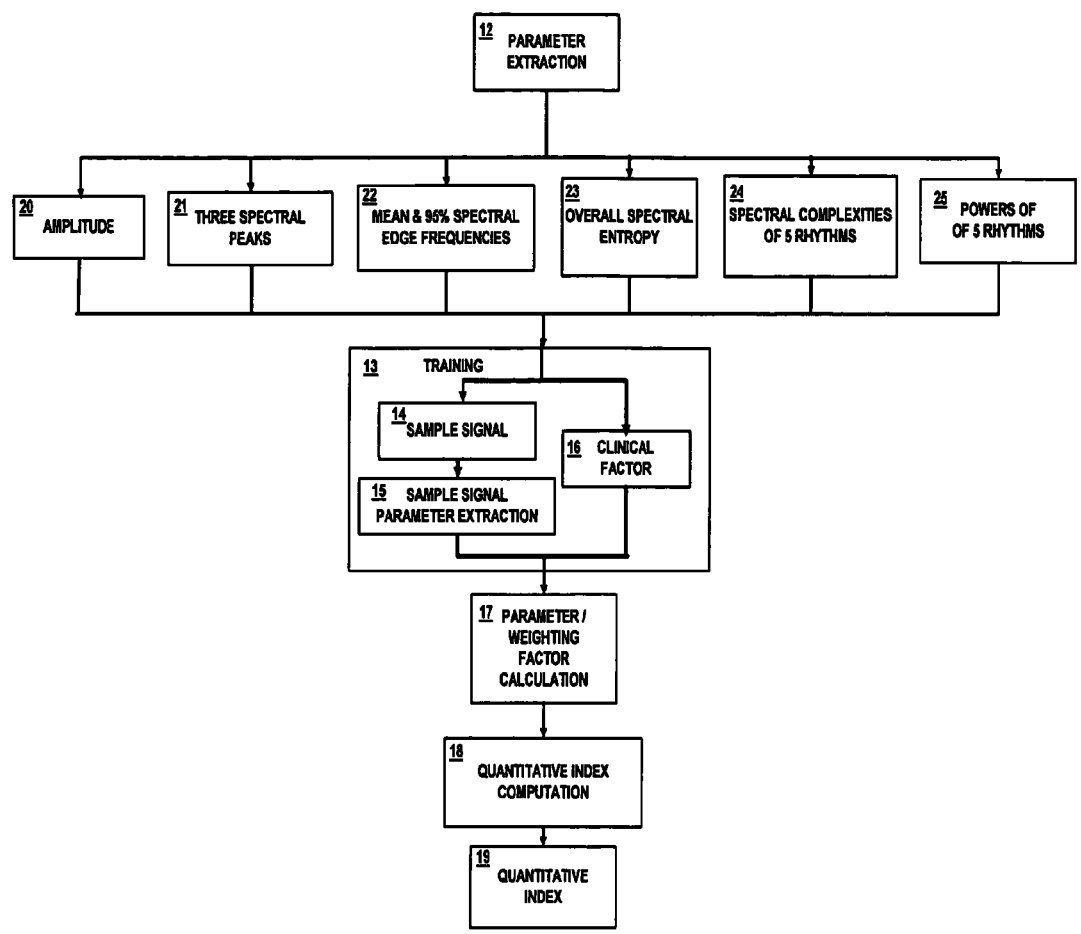
FIG. 7 specifies a set of EEG parameters chosen for neuronal injury detection and illustrates a schematic of combining the parameters with training to construct a quantitative index for neuronal injury detection, in accordance with certain embodiments.

The determination of the quantitative index may employ temporal, spectral, and probabilistic parameters. In certain embodiments, the plurality of parameters used in multi-parametric quantitative analysis may include but are not limited to amplitude, latency, frequency, entropy, power, and energy. FIG. 6 shows a set of specific EEG parameters selected to represent the status of brain in neuronal injury according to certain embodiments. A set of EEG parameters for neuronal injury may include, but are not limited to, amplitude 20, spectral peaks 21, mean and 95% spectral edge frequencies 22, overall spectral entropy 23, spectral complexities of five rhythms 24, and powers of five rhythms 25. These parameters are discussed in more detail below.

1. Amplitude 20: Reduction of EEG amplitude is correlated with neuronal injury. In certain embodiments, the normalized amplitude of the EEG signal may be one of the parameters used to generate the quantitative index. An amplitude related parameter may be computed as the mean of the absolute value of the normalized EEG signal amplitude (normalized to the maximum value) within each window.

2. Spectral peaks 21: In certain embodiments, Autoregressive (AR) Spectral modeling provides a capability to break down the EEG signal into a number of dominant frequency bands. The peak power levels in these dominant frequencies are indicative of brain injury and the uniform return of EEG activity in the three dominant frequency bands is indicative of a good recovery. Thus, three dominant frequency peaks may be included in the analysis to quantify uniform recovery in the dominant frequency bands.

3. Mean and 95% Spectral Edge Frequencies 22: Suppression of high frequencies has been correlated with brain injury. The power of each of the clinical rhythms (e.g. alpha, beta, gamma, delta, and theta) and the mean and 95% spectral edge frequencies (SEF) may be employed in certain embodiments to detect this. The mean and 95% SEF also allow detection of changes to the spectral distribution as a function of frequency due to brain injury or recovery.

4. Spectral Entropy: Changes in entropy may correlate with neuronal injury. Thus, in certain embodiments, sub-band and overall spectral entropy 23, spectral complexities 24, and powers of five rhythms 25 may all be included as parameters of interest in quantifying the numerical index.

Figure 8:
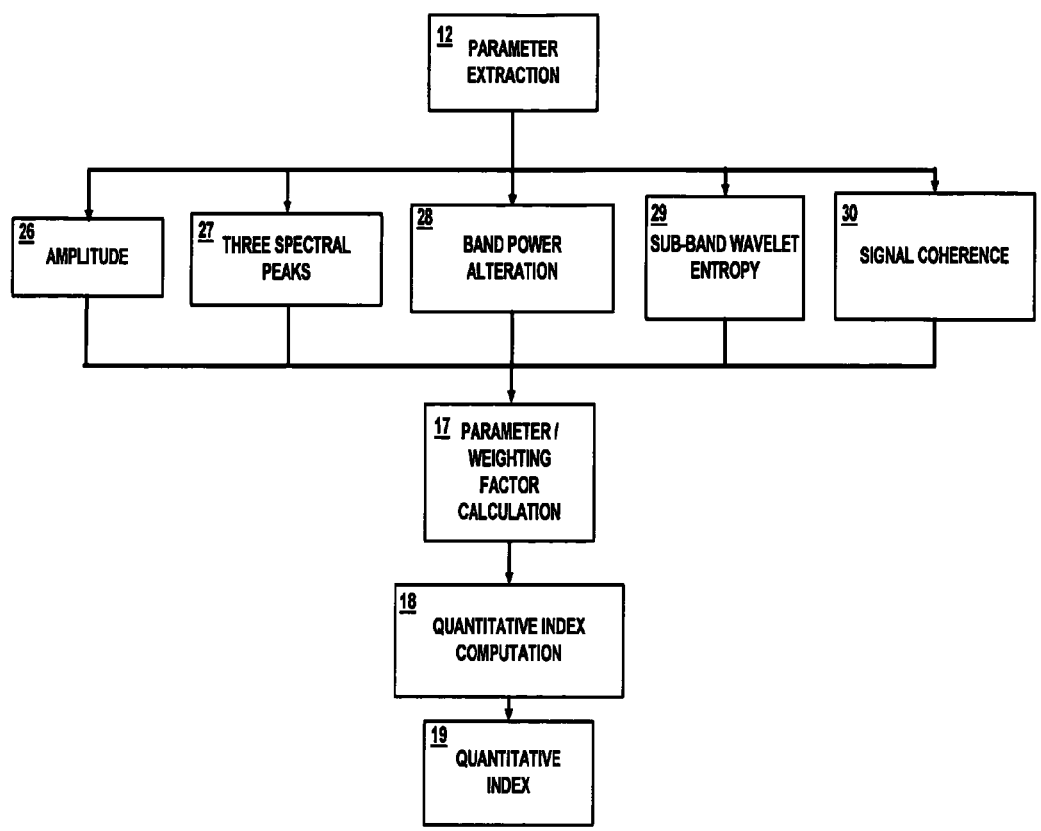
FIG. 8 specifies a set of EEG parameters for seizure detection and illustrates a schematic of combining the parameters to construct a quantitative index for seizure detection, in accordance with certain embodiments.

Thus, the quantitative index may integrate a selected set of specific parameters of the EEG which are affected by specific brain injury mechanisms. Note that for each condition being monitored, different sets of parameters may be used to optimize the performance of the quantitative index. For example, while both neuronal injury and seizure cause changes in EEG signals, the changes due to neuronal injury are different from those caused by seizure. Therefore, for maximal effectiveness, the set of specific parameters chosen for seizure and neuronal injury will logically be different. FIG. 8 specifies a set of EEG parameters selected for seizure detection according to certain embodiments. The EEG parameters selected for seizure detection in FIG. 8 include, but are not limited to, amplitude 26, three spectral peaks 27, band power alteration 28, sub-band wavelet entropy 29, and signal coherence 30. Note that this set of EEG parameters is different from the set of parameters selected for neuronal injury as illustrated in FIG. 6.

Figure 2:
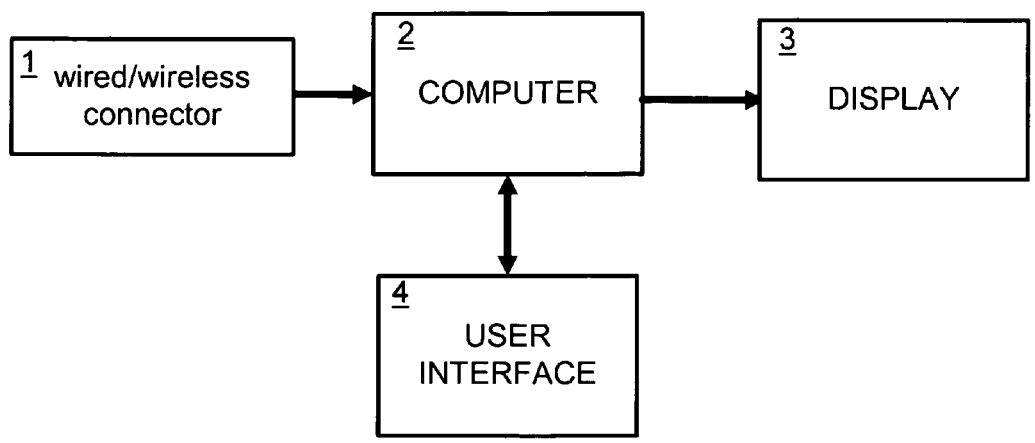
FIG. 2 illustrates a flow chart of a method for quantification of bioelectrical signals, in accordance with certain embodiments.

Referring to FIG. 2, an apparatus embodiment of the present invention is related to a signal data analysis method and system. The signal from a subject is acquired via a wired or wireless connector 1 and processed and stored in the system computer 2. The method parameters are input from a user interface 4 or are set/stored programmatically. The output of the method (the numerical index) is displayed on a graphics display 3 and/or are stored in the computer 2 (the graphics display 3 and computer 2 may be part of the same unit or may be separate units).

A method for processing the signal is described below and is shown in the flow chart illustrated in FIG. 3. The raw signal is obtained from the subject and is segmented into windows of a pre-set size. The signal is checked for artifacts using threshold-based artifact detection. Windows where the signal exceeds the threshold are discarded. The windowed data is then filtered by a band-pass filter and the amplitude of the signal is recorded.

The computer 2 receives the signal from the patient via wired or wireless connector or other means of transmission 1. As illustrated in the flowchart in FIG. 3, appropriate hardware filtering, amplification and time decimation of the signal 5 are performed in box 6. Windowing of the signal is realized in box 7, as follows. The signal window, $X(n)$, is given by the current sample and the $(T-1)$ previous samples $$X(n)=[x(n-T+1), x(n-T+2), \ldots, x(n)],$$

where T is the window size in samples given by $T=\tau(\text{sec})\times Fs$ (samples/sec). The number n is selected as $n=T, T+(T-d), T+2(T-d), \ldots$, where d is the number of the overlapped samples (taken zero here). This implies that each new window is obtained by sliding the previous window by $(T-d)$ forward in time.

Figure 4:
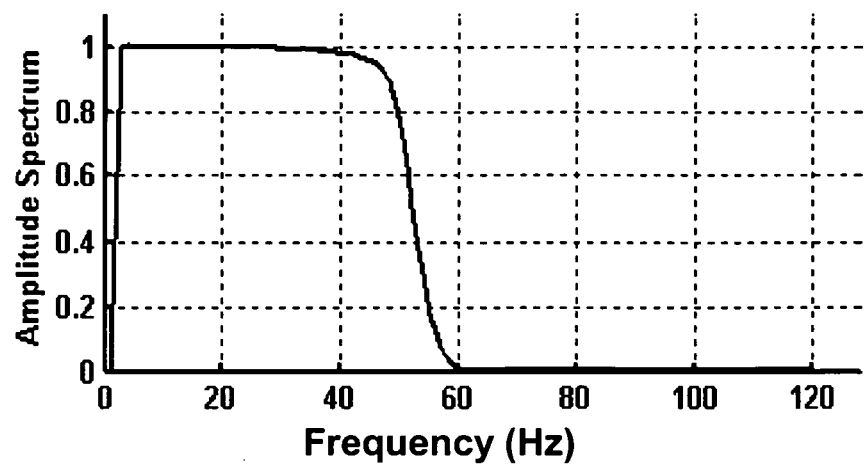
FIG. 4 illustrates the transfer function of a band-pass filter in accordance with certain embodiments.

Enhancement of the signal through noise and artifact removal is achieved in box 8, which includes boxes 9 and 10. Windows containing artifacts are rejected in box 9. A band-pass filter 10 is employed for removing of the out-of-band noise. The magnitude of the transfer function for an example band-pass filter is shown in FIG. 4.

In certain embodiments, an amplitude related parameter is employed for detecting the signal amplitude for each window and trends for successive windows. An amplitude related parameter can be computed as follows.

$$\frac{1}{T}\sum_{m=n-T} |x(m)/\max(x(m))|$$

Each window may be modeled using a $6^{th}$-order autoregressive model and the all-poles power spectral density is computed. The power spectral density is pass filtered and normalized such that its sum is equal to one.

Computation of the power spectrum is realized by box 11. In the autoregressive model based method, the signal is modeled as the output of a system with unknown coefficients whose input is white noise. The coefficients $\{1, a_1(n), a_2(n), \ldots, a_P(n)\}$ for the poles of the P-th order autoregressive system are then estimated for each signal window, $X(n)$, using an appropriate method, such as Burg's method. The direct form of a linear predictor can be used for the realization of Burg's method, but an all-zero lattice structure is more efficient due to its orthogonalization property. The poles of the autoregressive model are computed as the roots of the polynomial $$(1+a_1(n)z^{-1}+a_2(n)z^{-2}+\ldots+a_P(n)z^{-P}).$$

The poles whose frequencies are out of the desired band are eliminated and the remaining coefficients are used to reconstruct the signal. The power spectral density is computed based on the relevant autoregressive coefficients and can be written as $$H(f, n) = \frac{1}{\left|1 + \sum_k \tilde{a}_k(n)\exp(-j2\pi f)\right|^2}$$

where $\tilde{a}_k(n)$ are the coefficients and f is the normalized frequency given by $f=[0:\Delta f:(0.5-\Delta f)]$. The normalized frequency increment $\Delta f$ is obtained by 0.5/number of frequency bins. If the number of frequency bins is 512, this yields a frequency resolution of 0.25 Hz for a sampling frequency of 256 Hz. A subroutine is used to search for the fundamental spectral peaks. The power spectral density of the signal is normalized so that its sum (the total power) is equal to unity. The normalized power spectral density of the signal is given by $$\tilde{H}(f,n)=H(f,n)/\Sigma_f H(f,n)$$

The power spectral density associated with each signal window may also be computed starting with the Fast Fourier Transform (FFT) or another appropriate technique.

Figure 3:
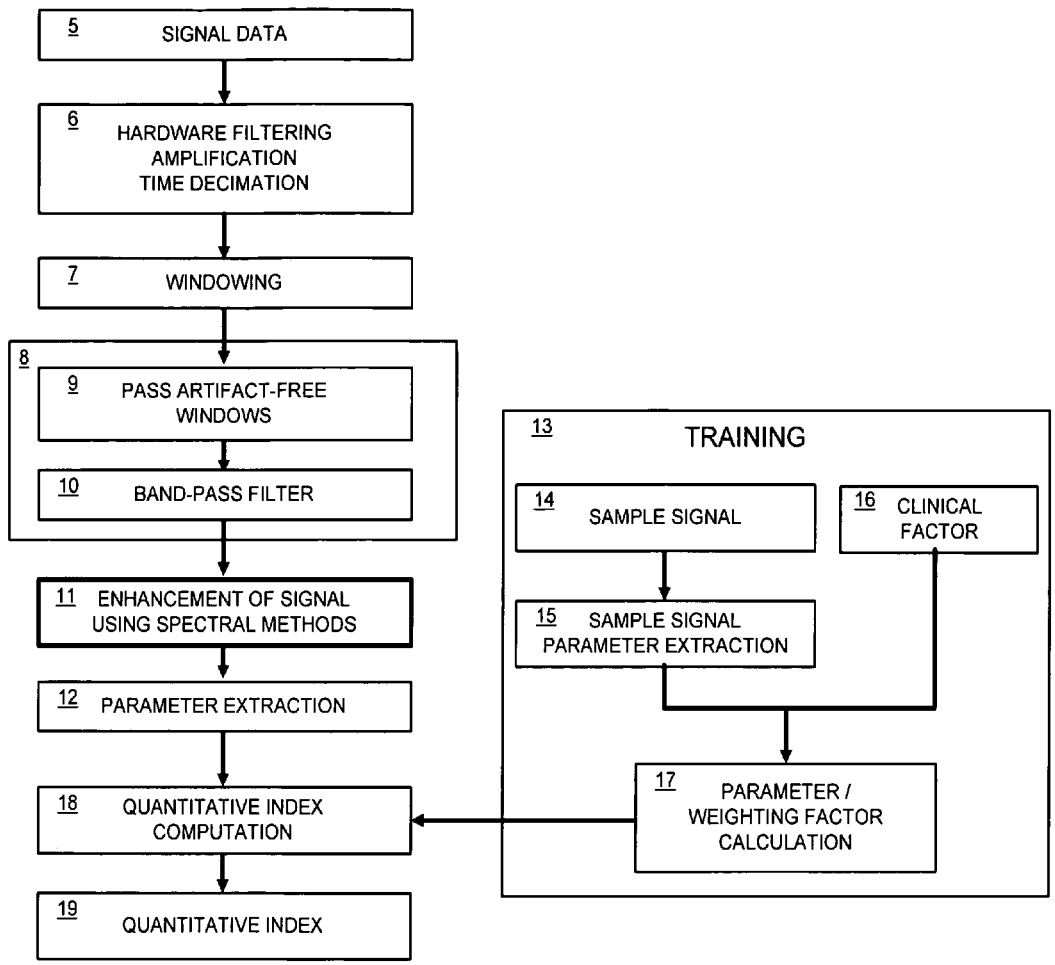
FIG. 3 illustrates a flow chart of a multi-parametric quantitative analysis method in accordance with certain embodiments.

The parameters of the signal are extracted in box 12 from the enhanced signal in box 11 (FIG. 3). In certain embodiments where the signal is a EEG signal, using the resultant normalized AR spectrum, the three fundamental spectral peaks 21, the mean spectral frequency and the 95% edge frequency 22 are computed along with the overall spectral entropy 23. The power spectral density is divided into the 5 clinical rhythms (i.e., alpha, beta, gamma, delta, and theta; or 1-4 Hz, 4-8 Hz, 8-13 Hz, 13-30 Hz, 30-50 Hz). The spectral entropy and power of each rhythm is also computed.

The spectral edge frequencies are computed from the normalized power spectrum. The overall spectral entropy 23 can be computed using different approaches, for example $$SE=\Sigma_f \tilde{H}(f,n)\log_2(\tilde{H}(f,n))$$

The normalized power spectral density is decomposed into relevant rhythms and sub-bands. The spectral entropy and the normalized power of these relevant rhythms are computed as follows.

$$SE_i(n)=\Sigma_f-\tilde{H}(f,n)\log_2(\tilde{H}_i(f,n))$$

$$p_i(n)=\Sigma_f\tilde{H}_i(f,n)$$

Figure 5:
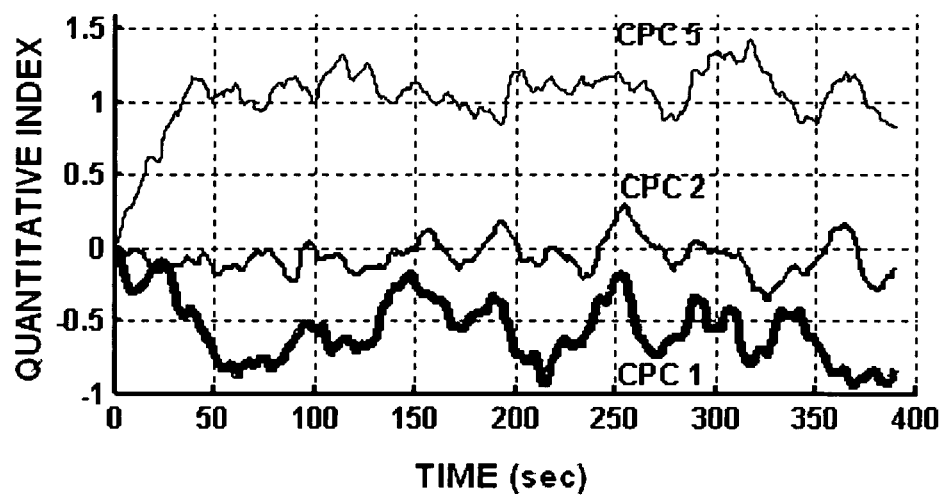
FIG. 5 illustrates graphical examples of quantitative index results for 3 neuronal injury levels in accordance with certain embodiments.

The quantitative index 19 may be computed as the weighted sum of the parameters. The weighting factors are pre-computed as described in the following section. The resulting quantitative index 19 can be displayed sequentially on a graphical display. FIG. 5 illustrates an embodiment of how different levels of brain injury may appear if superimposed on a single display. The three graphs of FIG. 5 each show the quantitative index as calculated over time. The graphs can be used to evaluate a condition of the patient. For example, the average value of the quantitative index over time can be correlated to a Cerebral Performance Category (CPC). The CPC is a known scoring approach for evaluating the neurological status of a subject. A CPC score of 1, for example, indicates a "good" neurological outcome, whereas a CPC score of 5 indicates a "poor" neurological outcome. As seen in FIG. 5, the lowest plot corresponds to a CPC of 1, the middle plot to a CPC of 2, and the upper plot to a CPC of 5.

The weighted combination of the signal parameters is computed in box 18 (FIG. 3). This can be thought of as a trained linear/nonlinear/neural network where the quantitative index 19 is the output and the combination of the parameters is the input. The weighting factors 17 of the trained system are obtained from training sample signals 14 and are stored in the system software.

The weighting factors 17 are computed by training the system using sample signals 14 with known corresponding quantitative values and the selected set of parameters. The sample signals 14 (training set) are processed as above. The resulting sample signal parameters 15 are combined with the known quantitative values to find the weighting factors 17.

In certain embodiments, training can be achieved adaptively using the least mean squares (LMS) algorithm or the recursive least squares (RLS) algorithm. Training may also be accomplished in batch fashion. Here, as an example, we present a linear system where the weighting factors 17 are adjusted using an adaptive least squares algorithm. The output at sample n is given by $$y(n)=F^t(n)W(n)$$

where d(n) is the desired value at each instant of time, F(n) is the parameter combination and W(n) is the weighting factor vector. The weights versus time is given by $$W(n+1)=W(n)-\mu[d(n)-F^t(n)W(n)]F(n)$$

The output at sample n+1 is then given by $$y(n+1)=F^t(n+1)W(n+1)$$

For a linear system, the parameters of each window of each sample signal 14 are computed. A parameter matrix, F, composed of the parameters of all windows of all examples is constructed. The desired vector, d, incorporates the numerical index values which correspond to the example signals. The linear system can then be written as Fw=d, where w is the weighting coefficient vector. Using the least squares criteria, the estimated weighting factor vector is given by the parameter matrix pseudo-inverse multiplied by the desired vector:

$$w=(F^tF)^{-1}F^td$$

where superscripts $^t$ and $^{-1}$ indicate matrix transpose and matrix inverse, respectively. The resulting vector w is then used with the parameter matrix from each window to calculate the numerical index value for each window.

In certain embodiments, the weighting factors 17 for each specific application and condition are established by training of a monitoring device, prior to first use, with a processing module 49 incorporating a code for multi-parametric quantitative analysis. In other embodiments, the training continues after the sale of the device in order to customize to a user's needs. In certain embodiments, this continual training may be achieved by inputting additional known sample signals from one or more subjects with a known condition. In certain embodiments, this continual training may be achieved by the user input of one or more clinical factors 16 in the form of a numerical value in a predetermined range. The user may also enter a clinical factor 16 in the categorical form (for example, good vs. bad vs. intermediate) which is then translated into a corresponding numerical value. The result is that the quantitative index 19 generated after training with clinical factors 16 will more closely reflect the user's own personal interpretation.

In certain embodiments where a clinical factor 16 is a clinician's impression based on visual interpretation of a bioelectrical signal, a clinician can enter his own impression, based on visual interpretation of a signal, in the form of a numerical value in a predetermined range. The clinician's numerical value will then be compared to the quantitative index 19. If the quantitative index 19 does not match the clinician's numerical value input, the weighting factors 17 may be adjusted using the clinician input so that when new weighting factors are applied to parameters extracted in box 12, the new quantitative index will match the clinician's numerical value input. This new weighting factors may be applied in the future, if the user so chooses, so that future quantitative index will more closely resemble a clinician's impression based on his own personal interpretation of a bioelectrical signal.

For example, in certain embodiments, an automated EEG machine may express the quantitative index 19 in the range of 0 to 100, which may correlate with the percentage of likelihood that a particular EEG signal 5 represents seizure activity. A clinician, after visual interpretation of the same EEG signal 5, may enter his own impression in the form of a numerical value for the likelihood that this EEG signal represents seizure activity. If the device-constructed quantitative index 19 differs from the clinician's numerical input, the weighting factor 17 may be adjusted so that the quantitative index will match the clinician's numerical input. This would enable a clinician to "tune" the device so that the quantitative index given by the device in the future will more closely resemble the clinician's own impression of a bioelectrical signal. As previously mentioned, a clinician may also have the option of entering categorical information, such as good vs. bad vs. intermediate, which is then translated into a numerical value for subsequent training.

In certain embodiments, a clinical factor 16 may be a patient's risk of having a particular condition. A clinician can enter his own clinical impression of risk for a particular condition in the form of a numerical value based on a patient's individual risk factors. This numerical value of risk is then used to adjust weighting factors 17 such that identical bioelectrical signals would result in different quantitative index values 19 in high risk vs. low risk patients. For example, the constructed quantitative index value from an EKG signal may represent the likelihood that a subject with implantable pacemaker or defibrillator is having myocardial ischemia severe enough to cause myocardial infarction. As used herein, electrocardiogram (EKG) includes signals obtained from electrodes positioned outside of the heart and/or signals obtained from electrodes positioned within the heart. Thus, signals obtained from body surface leads and signals obtained from intra-cardiac leads may both be considered EKG signals. If a physician feels that this individual subject is at a particularly high risk for myocardial infarction and would like to be notified even if the signal represents only moderate ischemia that is not severe enough to cause myocardial infarction, he may enter this high risk as a numerical value for training. During training, the weighting factors may be adjusted such that an EKG signal that otherwise results in an numerical index in the range of "moderate ischemia not severe enough to cause myocardial infarction" wound now be in the range of "ischemia severe enough to cause myocardial infarction". An alarm or other means of notification may then be triggered to alert the patient and medical personnel so much earlier intervention (rather than the normal time course of intervention for low-risk individuals) can be given to this high-risk patient to prevent progression into full-blown myocardial infarction.

In other embodiments, a clinical factor 16 may also include clinical information that is already in the form of a numerical value with established range indicating normal vs. abnormal conditions. These clinical factors include established clinical scoring system such as Glascow Coma Scale (GCS), APGAR score for neonates, coronary artery disease assessment score, Cerebral Performance Category (CPC), Fugl-Meyer assessment (FMA), modified Ashworh scale (MAS), and manual muscle test (MMT) scores. Other embodiments may use other numerical clinical factors including, but not limited to vital signs, tissue oxygen saturation, and laboratory results of bodily fluids and tissues. Vital signs include, but are not limited to, heart rate, temperature (both natural core temperature and brain temperature during hypothermia treatment), respiratory rate, blood pressure, central venous pressure, pulmonary wedge pressure, and intracranial pressure (ICP). The laboratory values may include, but are not limited to, anti-seizure medication level, creatine kinase-BB isoenzyme, neurone-specific enolase, astroglial protein S-100, creatine kinase-MB, troponin, and myoglobin levels. Bodily fluids may include, but are not limited to, blood, serum, cerebrospinal fluid (CSF), urine, peritoneal fluid, and sputum. While the embodiments described above use EEG and EKG as examples, the same method for generating a quantitative index from either bioelectrical signals alone or in conjunction with other clinical factors may apply to all modes of bioelectrical signals.

Certain embodiments relate to a single or multiple channel method for quantitative analysis and monitoring of bioelectrical signals. A quantitative analysis of bioelectrical signals 5 and the resulting quantitative index 19 may find use in diagnosis/monitoring/classification of various cerebral activities and brain dysfunctions. These include, but are not limited to, cortical brain injury post cardiac arrest, assessment of the impact of therapeutic hypothermia and other brain injury treatments, epilepsy and seizure detection and prediction, sleep disorders analysis, Alzheimer's early-detection, depth of anesthesia, traumatic brain injury, stroke and subarachnoid hemorrhage (SAH), brain computer interface (BCI) and other EEG based (and non-EEG-based) quantitative diagnosis/classification of cerebral activities.

The quantitative index generated from multi-parametric analysis of single channel and multiple channel bioelectrical signals may have a wide range of clinical uses. In certain embodiments, hypoxia can be detected by examining changes in bioelectrical signals. Hypoxia occurs when the supply of oxygen is not enough to meet tissue demands, leading to injury or death of cells. Hypoxia can occur due to lack of oxygen in blood in the presence of normal circulation such as in patients who having difficulty breathing. Hypoxia can also occur due to the lack of blood flow. A global lack of blood flow occurs during cardiac arrest. Regional lack of blood flow can occur as a consequence of blood clot obstructing blood flow to a particular area such as in heart attack or ischemic stroke. Regardless of its different causes, hypoxia results in cell injury and death, resulting in changes in cell electrophysiology. By examining the bioelectrical signals, these changes can be detected and analyzed to generate a quantitative index reflecting the condition of the cells. Therefore, this quantitative index can be used for computer based diagnosis of normal versus pathological conditions in certain embodiments. The quantitative index may also be used to monitor real-time status of disease states and monitor the response to treatment in certain embodiments. Furthermore, the quantitative index can be used to identify the modality of treatment, magnitude of treatment, dosage of treatment, and timing of treatment according to certain embodiments.

In addition to hypoxia, other mechanisms can also cause neuronal injury or death. Intracranial mass lesions can cause compression on surrounding brain tissue, leading to neuronal injury or death in the surrounding tissue. Intracranial mass may include but are not limited to blood clot after cerebral hemorrhage such as in hemorrhagic stroke, abscess, and tumor. Traumatic brain injury is another mechanism causing neuronal injury or death. Alzheimer's disease, where amyloid is deposited and causes cell dysfunction, is another mechanism which leads to neuronal injury and death. Hydrocephalus is a condition in which cerebral spinal fluid (CSF) accumulates in the brain. Since cranial cavity is rigid and cannot expand, the accumulation of CSF causes increased intracranial pressure (ICP), which in turns causes compression of brain tissue and lead to neuronal injury and death. Therefore, the set of parameters chosen for neuronal injury will generally apply to certain embodiments involving using the quantitative index to detect stroke, intracranial mass lesions, traumatic brain injury, hypoxia, and hydrocephalus.

Bioelectrical signals from the brain also have distinct characteristics during different states of consciousness. For example, the brain signals from an awake subject is very different from a sleeping subject. Normal sleep also has different signal characteristics from abnormal sleep. Therefore, the quantitative index may be used to detect sleep disorder. The bioelectrical signals from the brain also undergo changes with anesthesia. As anesthesia deepens, the subject gradually loses life-saving reflexes such as the breathing reflex and gag reflex. During surgery, the depth of anesthesia must be deep enough to control pain and suppress reflexes that may interfere with surgical procedures. However, the depth of anesthesia must be light enough that the subject can wake up quickly at the end of the surgery resume spontaneous breathing. Therefore, the quantitative index may be used in certain embodiments to detect and monitor depth of anesthesia.

When cardiac arrest victims are successfully resuscitated, over 80% are comatose for a period of time. Many of the comatose patients end up in persistent vegetative state or death. However, clinicians currently have very limited ability to predict which patients will wake up and be neurologically functional. Today, one typically waits for these comatose patients to wake up: the sooner they wake up, the better the neurological outcome. The inventors have discovered that the quantitative index 19 constructed from EEG signal 5 recorded within 48-72 hours after cardiac arrest, when patients are still comatose, can predict neurological outcome of cardiac arrest survivors at the time of hospital discharge several weeks later. FIG. 5 demonstrates a graphical display of quantitative index in relation to neurological outcome at hospital discharge, the Cerebral Performance Category (CPC). CPC 1 patients are fully functional after awakening from coma; and CPC 5 patients have poor neurological outcome. Therefore, the quantitative index can be used in certain embodiments to predict neurological outcome according to certain embodiments.

Hypothermia has emerged as a promising treatment to inhibit further neuronal injury to the brain after reestablishment of blood flow after cardiac arrest. However, monitoring the brain's response to treatment by bedside clinical exam is of limited value in comatose patients. Since we have selected a specific set of parameters (amplitude 20, three spectral peaks 21, mean & 95% spectral edge frequencies 22, overall spectral entropy 23, spectral complexities of 5 rhythms 24, and powers of 5 rhythms 25) to construct the quantitative index reflecting the status of neuronal injury, as described above, this quantitative index can also be used to monitoring response to hypothermia and other treatment modalities according to certain embodiments.

In one embodiment, the numerical index generated form multi-parametric quantitative analysis of a bioelectrical signal can be used in the operating room to monitor depth of anesthesia. In another embodiment, the quantitative numerical index of a bioelectrical signal, such as an evoked potential, is used to prevent surgical injury to nerves and important areas of the brain intra-operatively. In another embodiment, this numerical index can be used for seizure detection and response to anti-seizure treatments. In an additional embodiment, the numerical index can be use in detection of cardiac ischemia and arrhythmia. In other embodiments, the quantitative index may be used for diagnosis of antenatal hypoxia (lack of oxygen of a fetus before birth). This quantitative index can be used to diagnose antenatal hypoxia both in mature fetus (gestational age of 37 weeks or greater) and premature fetus (gestation age less than 37 weeks). This quantitative index may also find use in monitoring fetus during labor to help doctors decide when to intervene.

Figure 22:
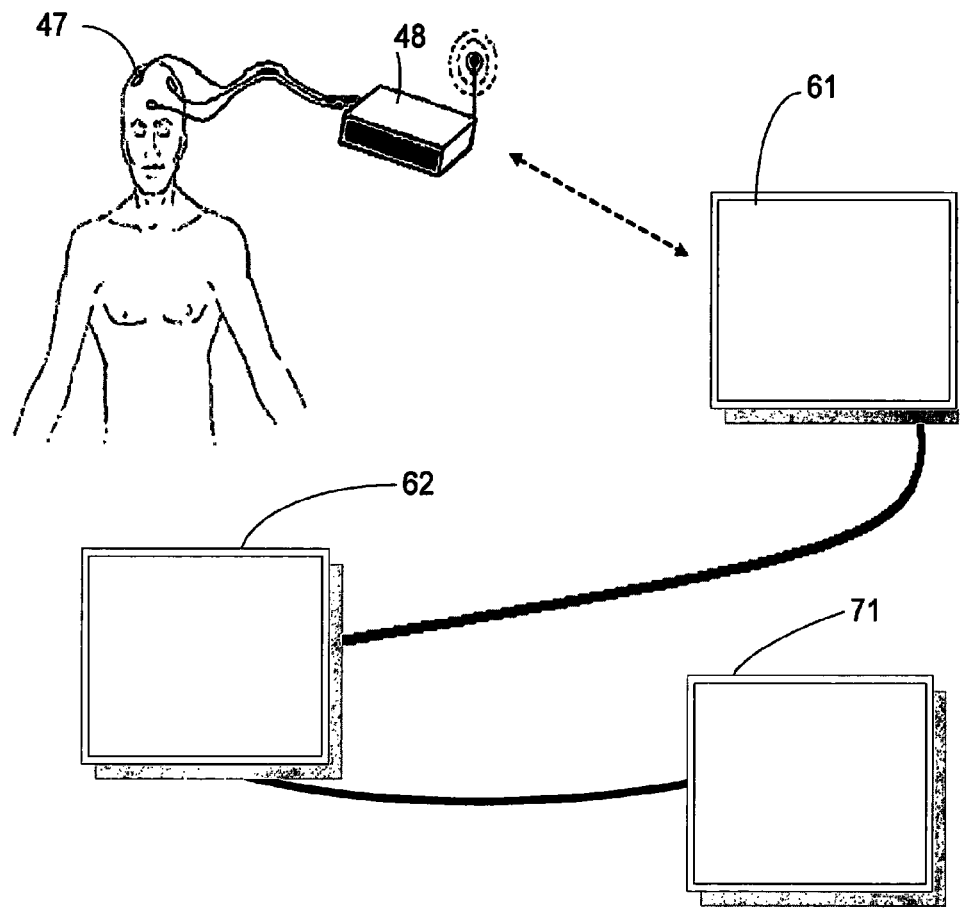
FIG. 22 illustrates a brain computer interface in accordance with certain embodiments.

Furthermore, bioelectrical signals can be used to determine the intent of a subject, allowing the subject to operate a computer under brain control 62 or a device 71 in the manner of brain-computer interface according to certain embodiments (FIG. 22). Certain embodiments involve the use of the quantitative index to express a subject's intent to operate the computer under brain control 62 or the device 71. Intent is a deliberate cognitive process. However, in a recording of bioelectrical signals, the signals corresponding to intent are typically buried amongst a vast amount of other random signals. In order to use a signal corresponding to intent, one must first identify and distinguish it from all the other random signals. Using the multi-channel evoked potential as an example, if we monitor evoked potential to identify intent, we need to separate out meaningful EP corresponding to intent from a background of other random EEGs and normative EP responses (the common mode response). An EP signal corresponding to intent may have a later latency (for example, P300 at 300 msec) and also may have a different shape, allowing us to use these parameters to separate an EP corresponding to intent from all the other background EPs. The multi-parametric approach may be used to identify the EP signal corresponding to intent across multiple channels against a background of other random EPs, extracts the signal parameters 12, and construct a quantitative index 19 representing the intent. The numerical value of quantitative index 19 may then be used to determine an instruction to perform an action by the device 71 or the computer under brain control 62 according to certain embodiments. For example, the instruction for an action may be physically moving a prosthetic arm, if the device 71 is a prosthetic arm. A subject's intent in the form of a bioelectrical signal may be recorded and analyzed using the multi-parametric approach, resulting in the quantitative index 19. Once the quantitative index 19 is generated, the particular numerical value of the quantitative index 19 may be used to assign a particular instruction to the prosthetic arm, such as moving the arm to the left if the numerical value is a positive number, and moving the prosthetic arm to the right if the numerical value is a negative number. Alternatively, the instruction to the prosthetic arm may also be expressed by a predetermined numerical range, such as moving the arm up if the numerical value is in the range of 50 to 100, and moving the arm down if the numerical value is from 0 to 49. Similarly, the quantitative index 19 may also be used to give a instruction to the computer under brain control 62 according to certain embodiments.

The quantitative index 19 can also be modified by training 13 in order to customize the brain-computer-interface to individual user differences, according to certain embodiments. For example, a subject's EP corresponding to intent may be different under various conditions. EP responses occurring under conditions of habituation, such as in a repetitive motor task or during periods of fatigue, may be different from normal EP responses without fatigue. This difference may affect a subject's ability to communicate his intent to the device 71 or the computer under brain control 62. Also, there may be individualist differences in EP signals from one subject to the next, resulting in different intrinsic ability of subjects to communicate intent to the device 71 or the computer under brain control 62. While a subject may overcome this by learning to modulate his own EP responses with repeated practice to learn to better control the device 71 or computer 62, certain embodiments may utilize an alternative approach to use the subject's own EP response as sample signals 14 to adjust the weighting factor 17 during training 13. The resulting quantitative index 19 will then effective control the device 71 or the computer under brain control 62 without repeated practice by individual subjects.

Figure 9:
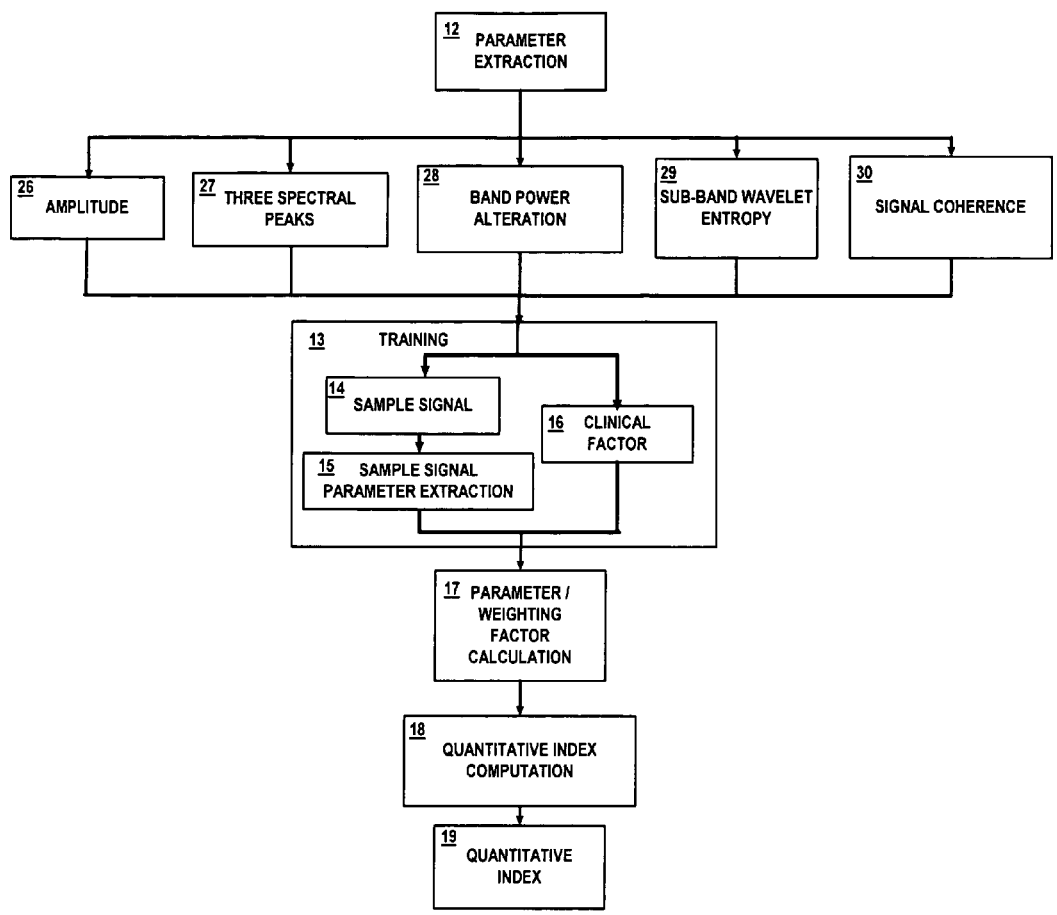
FIG. 9 specifies a set of EEG parameters for seizure detection and illustrates a schematic of combining the parameters with training to construct a quantitative index for seizure detection, in accordance with certain embodiments FIG. 10 specifies a set of EP parameters and illustrates a schematic combination of the parameters to construct a quantitative index, in accordance with certain embodiments.

In addition to neuronal injury detection, EEG signals may also detect seizure in certain embodiments. When EEG is used to detect seizure activity, a preferred set of specific parameters may be different from the set chosen for neuronal injury. FIG. 8 specifies a set of EEG parameters chosen for seizure detection may include, but are not limited to, amplitude 26, three spectral peaks 27, band power alterations 28, sub-band wavelet entropy 29, and signal coherence 30. FIG. 9 illustrates that construction of quantitative index 19 using EEG seizure signals may include training via either sample signal 14, clinical factor 16, or both, to adjust weighting factors 17 to yield a quantitative index 19.

1. Amplitude 26: Increase in amplitude of EEG signals typically occurs with the onset of seizures. In certain embodiments, the normalized amplitude of the EEG signal may be one of the parameters used to generate the quantitative index. An amplitude related parameter may be computed as the mean of the absolute value of the normalized EEG signal amplitude (normalized to the maximum value) within each window.

2. Spectral peaks 27: In certain embodiments, Autoregressive (AR) Spectral modeling provides a capability to break down the EEG signal into a number of dominant frequency bands. AR peaks become narrow as poles move toward the unit circle. Thus, three dominant frequency peaks may be included in the analysis to quantify seizure activity in the dominant frequency bands.

3. Band power alteration 28: With seizure activity, spectral widening occurs and larger proportion of signal moves to the higher frequencies. Delta activity increases with seizure. Large increases in the beta and gamma frequencies may also be seen.

4. Sub-band wavelet entropy 29: Sub-band wavelet entropy is a measure of band complexity. It generates a volatility measure for each band as well as power changes in the five bands.

5. Signal coherence 30: Signal coherence examines the level of periodicity in a signal. With a seizure event, the signal coherence would increase. Certain types of seizures are more periodic than others and would increase the periodicity more than other seizure waveforms. Entropy coupled with signal coherence allows for an intelligent decision on randomness and consistency in waveform descriptions.

In accordance with certain embodiments, specific parameter sets selected for different classes of bioelectrical signals, namely evoked potential (EP), electromyogram (EMG), EKG, will be described.

Figure 10:
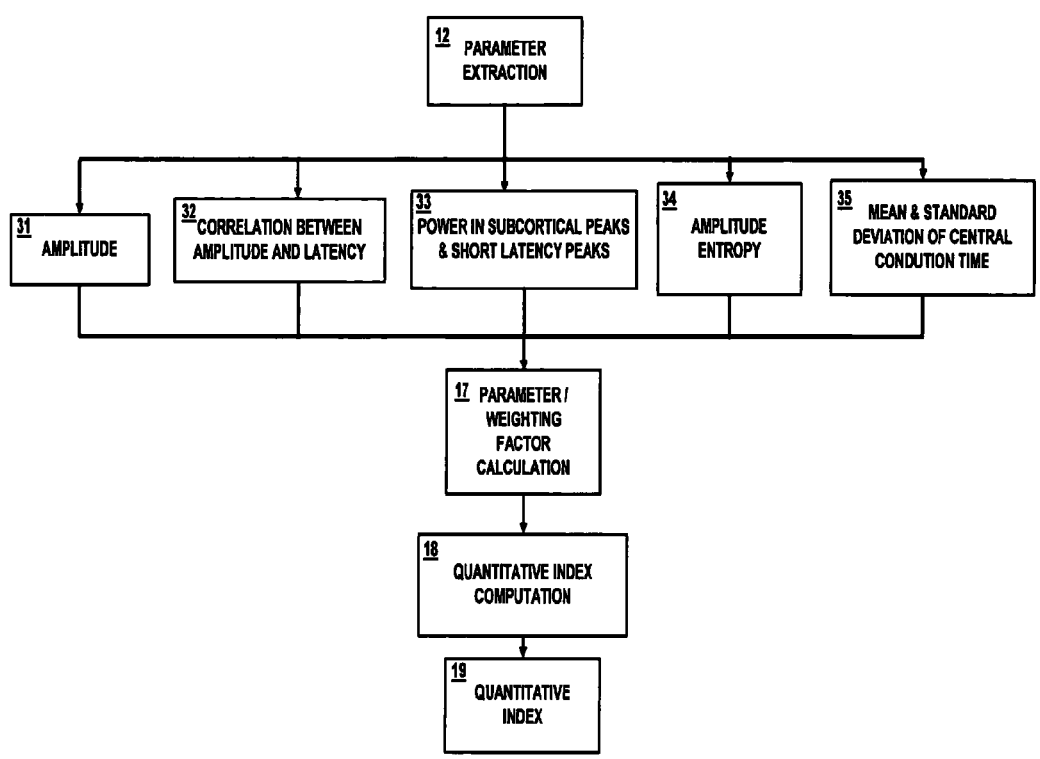

In embodiments where the signal is an evoked potential (EP), FIG. 10 illustrates that the same method described above may be used for EP to generate a quantitative index. The set of specific parameters selected for a EP signal may include, but are not limited to, amplitude 31, correlation of amplitude and latency 32, power within the subcortical peaks and short latency peaks 33, amplitude entropy 35, and mean and standard deviation of central conduction time 36. In certain embodiments, the peaks of EP signal used for parameter selection may include but are not limited to N13, N20, P25, and N35. In certain embodiments, N13 and N20 peaks are chosen for the diagnosis of hydrocephalus.

1. Amplitude 31: Amplitude of the waveform at certain latency reflects coordinated activity of anatomical structures in response to stimulation. In neuronal injury, the coordination between anatomical structures is compromised.

2. Correlation of amplitude and latency 32: This measures the synchronicity of amplitude and latency at any given time point in the EP signal.

3. Power within subcortical and short latency peaks 33: This is done by performing spectral decomposition of peaks. It measures the spread of latency for several peaks: N13-N20, and P25-P45.

4. Amplitude entropy 34: It measure the consistency of EP activity at a given time point in the signal. It provides the information content of significant wavelet scales of several peaks: N13, N20, P25, and P35.

5. Mean and standard deviation of central conduction time 35: This measure reflects the neural propagation time. In injury, this propagation time is prolonged. Therefore, it provides information about the integrity of neural tracts.

Figure 11:
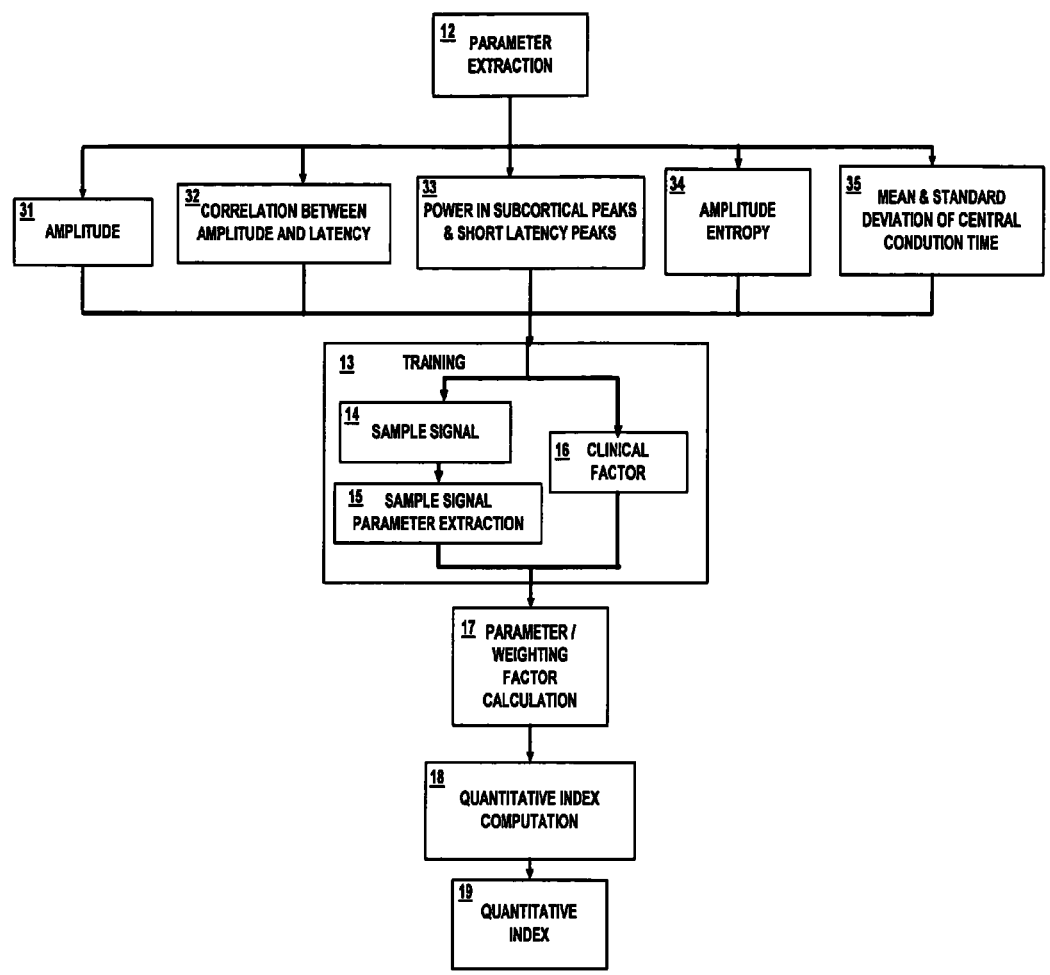
FIG. 11 specifies a set of EP parameters and illustrates a schematic of combining the parameters with training to construct a quantitative index, in accordance with certain embodiments.

FIG. 11 illustrates that construction of quantitative index 19 using EP signals may include training via either sample signal 14, clinical factor 16, or both, to adjust weighting factors 17 to yield a quantitative index 19.

In a manner similar to the methods previously described using EEG as an example, weighting factors can be influenced by training with user input of clinical information in certain embodiments.

Figure 12:
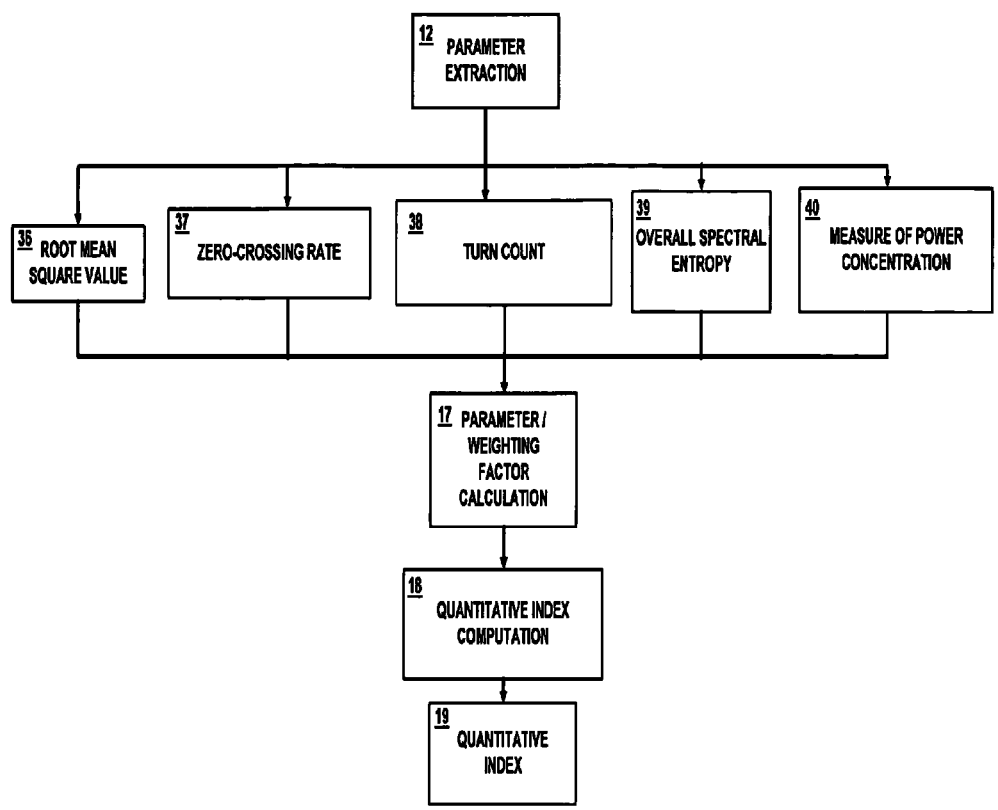
FIG. 12 specifies a set of EMG parameters and illustrates a schematic combination of the parameters to construct a quantitative index, in accordance with certain embodiments.

In the embodiments where a signal is an electromyogram (EMG), FIG. 12 illustrates that the same method described above may be used for EMG to generate a quantitative index. The set of specific parameters selected from an EMG signal may include, but are not limited to, root mean square value 36, zero-crossing rate 37, turns count 38, overall spectral entropy 39, and measures of power concentration 40.

1. Root mean square value 36: Root mean square value reflects the power of muscle activity. Increased muscular activity translates into more power.

2. Zero-crossing rate 37: Zero crossing rate is a measure of how "busy" the muscle is. More multiple unit action potentials (MuAPs) means more activity.

3. Turns count 38: Turns count measures every change in phase. It correlates with the number of spikes occurring in interference pattern. Subjects with myopathy have higher turn counts than normal subjects.

4. Overall spectral entropy 39: Entropy changes with injury. Muscle tremor has a regular and periodic pattern, resulting in decreased overall spectral entropy. Muscle spasms are random bursts in muscle activity, resulting in increased overall spectral entropy.

5. Measures of power concentration 40: Measures of power concentration reflects activity level and the responsiveness of muscle by examining the median and mean frequencies and bandwidth of the spectrum. It discriminates fast vs. low muscle activities.

Figure 13:
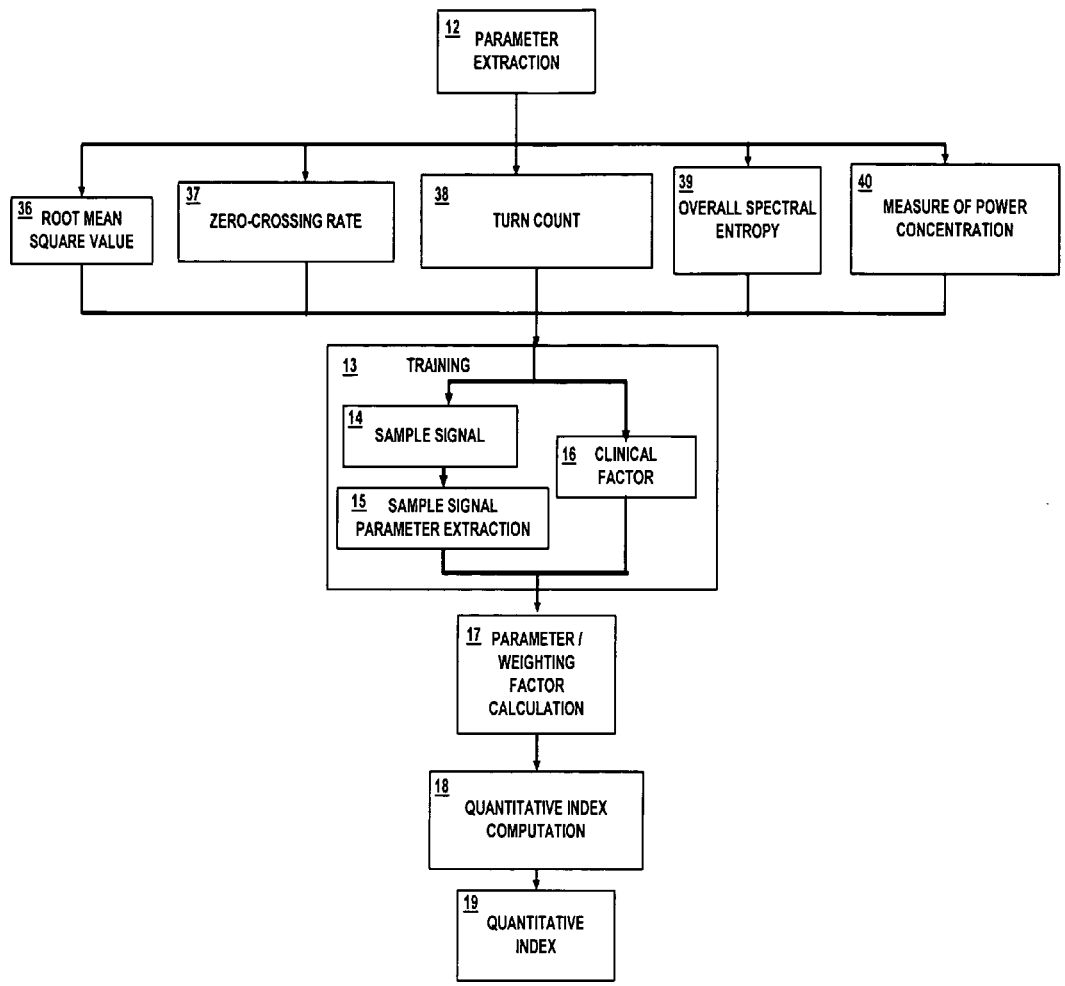
FIG. 13 specifies a set of EMG parameters chosen and illustrates a schematic of combining the parameters with training to construct a quantitative index, in accordance with certain embodiments.

FIG. 13 illustrates that construction of quantitative index 19 using EMG signals may include training via either sample signal 14, clinical factor 16, or both to adjust weighting factors 17 to yield a quantitative index 19

Figure 14:
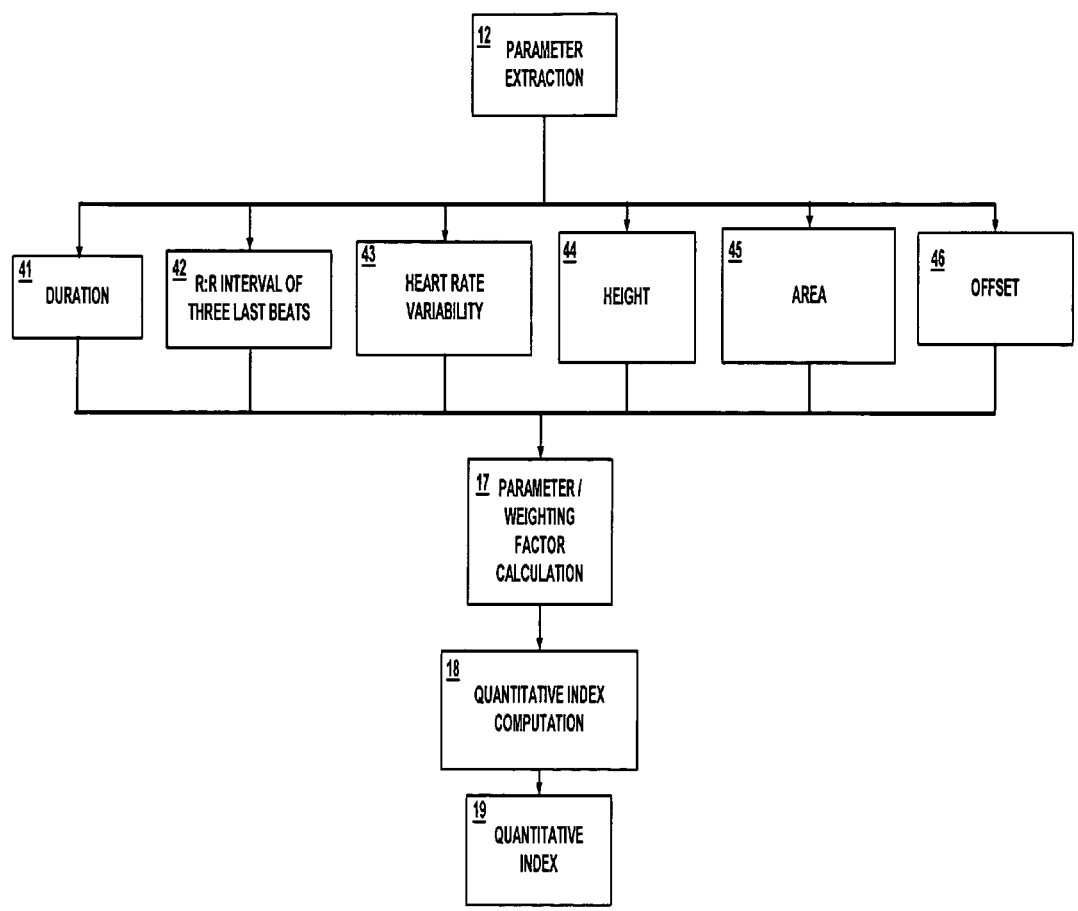
FIG. 14 specifies a set of EKG parameters and illustrates a schematic combination of the parameters to construct a quantitative index, in accordance with certain embodiments.

In the embodiments where a signal is an EKG signal, FIG. 14 illustrates that the same method described above may be used for an EKG signal to generate a quantitative index. Similar to other bioelectrical signals, a multi-parametric approach utilizing temporal, spectral and probabilistic parameters can be applied to EKG signals to generate a quantitative index. The set of specific parameters selected from an EKG signal, shown in FIG. 14, may include, but are not limited to, duration 41, R:R interval of three last beats 42, heart rate variability 43, height 44, area 45, and offset 46.

1. Duration 41: This refers to the duration of the QRS complex. This is the time it takes to complete one cycle of depolarization at AV node.

2. R:R interval of last three beats 42: R:R interval is the time it takes to complete a heart cycle. By examining the R:R interval of the last three beats, we can measure the beat-to-beat uniformity in the three dominant frequencies.

3. Heart rate variability 43: It measures the consistency of heart rate by examining R:R interval variability.

4. Height 44: This is determined by taking the difference between the maximum and minimum amplitude of QRS complex.

5. Area 45: This is the area under the QRS waveform rectified with respect to a straight line through the midpoint of the baseline. The baseline is defined as the straight line connecting the temporal boundary points of the QRS complex. The center is defined as the midpoint between the highest and lowest bounds in the amplitude of the QRS complex.

6. Offset 46: This is the positive or negative vertical distance from the midpoint of the baseline to the center of the QRS complex. It measures the depolarization level change.

Figure 15:
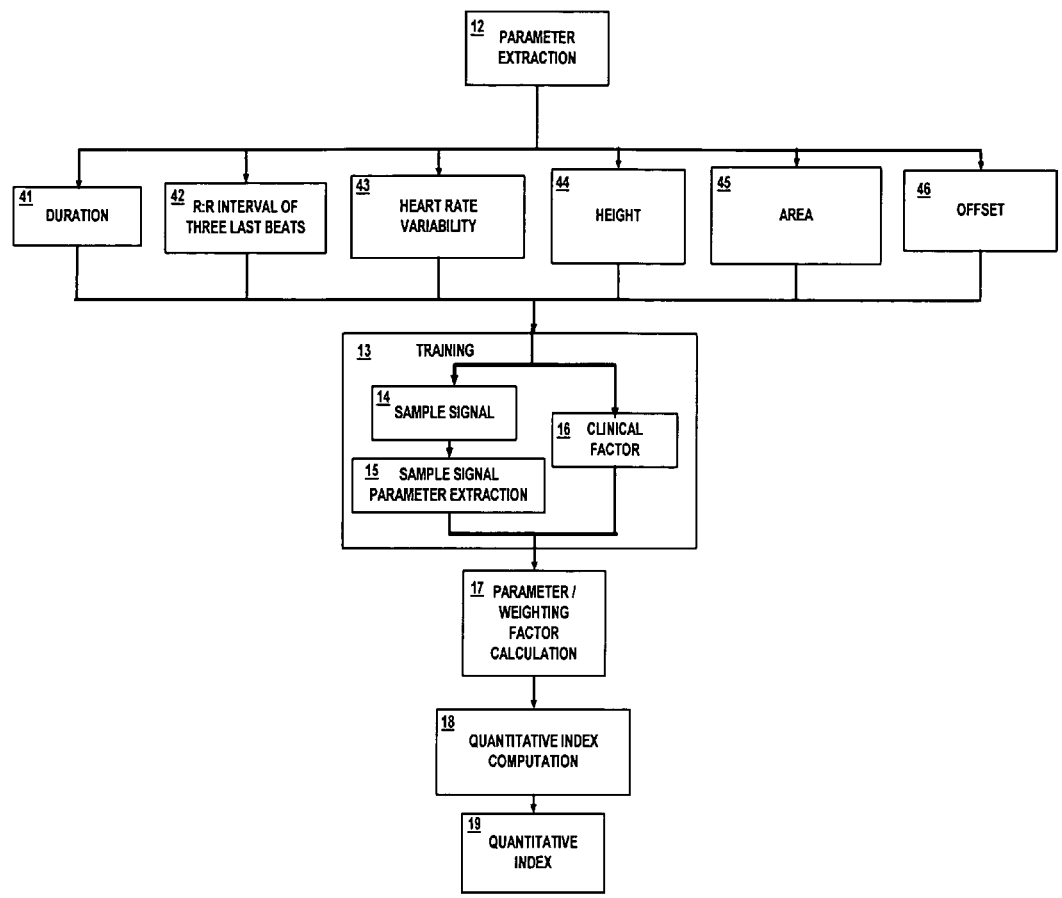
FIG. 15 specifies a set of EKG parameters and illustrates a schematic of combining the parameters with training to construct a quantitative index, in accordance with certain embodiments.

FIG. 15 illustrates that construction of quantitative index 19 using EKG signals may include training via either sample signal 14, clinical factor 16, or both, to adjust weighting factors 17 to yield a quantitative index 19.

The quantitative index constructed from EKG signals may be used to cardiac arrhythmia in certain embodiments. By selecting a set of parameters which best represents variability in heart rate, the quantitative index can detect cardiac arrhythmia. Cardiac conduction defect/delay can also be detected by the quantitative index in certain embodiments by examining parameters focused on conduction time across different channels. Myocardial ischemia and myocardial infarction can also be detected by multi-parametric analysis of the EKG signal according to certain embodiments. The classification of myocardial ischemia vs. myocardial infarction is frequently one of degree: mild to moderate myocardial ischemia which leads to myocardial cell injury which can be reversed upon establishment of adequate blood flow. Myocardial infarction occurs myocardial ischemia becomes so severe that myocardial cells die. Since myocardial cells cannot regenerate, the myocardial cell death is irreversible and permanent once infarction occurs. The quantitative index is well-suited for the diagnosis of myocardial ischemia vs. infarction due to its ability to quantify severity of injury.

Two or more modes of bioelectrical signal (i.e. EEG, EMG, EP, EKG) can be used together to generate one single comprehensive quantitative index according to certain embodiments. In certain embodiments, simultaneous recording of EEG signals and EP signals can be used to monitor the overall neurological status of a subject. One example uses simultaneous recording of EP and EEG signals are used to predict neurological outcome, monitor brain's recovery, and assess response to hypothermia treatment in comatose patient after cardiac arrest. In another embodiment, EP and EMG may be used concurrently to generate one single comprehensive quantitative index which reflects the overall status of neuromuscular system. In yet another embodiment, EP, EEG, and EMG can be simultaneously used together to yield a comprehensive quantitative index which reflects the overall status of the entire neurological and neuromuscular system. In one further embodiment, EKG is combined with any combination of the signals (EEG, EMG, EP) to yield an index reflecting the overall clinical status of the subject.

In other embodiments, additional clinical factor 16 including risk factor, clinical scoring systems, vital signs, and laboratory value may also be added to any combination of bioelectrical signals to generate a comprehensive quantitative index 19.

Figure 16:
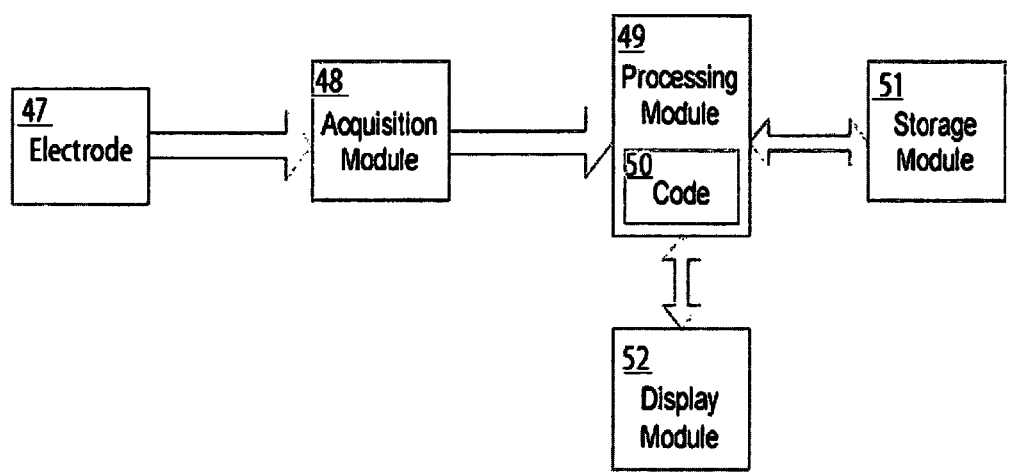
FIG. 16 illustrates a schematic of the hardware components in a bioelectrical signal monitoring system in accordance with certain embodiments.

Some of the hardware embodiments which incorporate a processing module embedded with a code for constructing the quantitative index from bioelectrical signals are described below. FIG. 16 shows a schematic of a bioelectrical signal monitoring system according to certain embodiments. The central component of the monitoring system is a processing module 49 embedded with a code 50 which utilizes the multi-parametric quantitative analysis to construct a quantitative index which corresponds to a subject's condition. Electrodes 47 collects the bioelectrical signals and transmit them to an acquisition module 48 via either wired or wireless connection. The acquisition module 48 in turn transmits the signal to the processing module 49, which is in communication with a storage module 51 capable of storing data in memory. The code 50 constructs the quantitative index and transmits it to a display module 52 for graphical display. The connection between the electrodes 47, the acquisition 48, the processing module 49, the storage module 51, and the display module 52 may be via wires, wireless connectors, or other means of communication.

Figure 17:
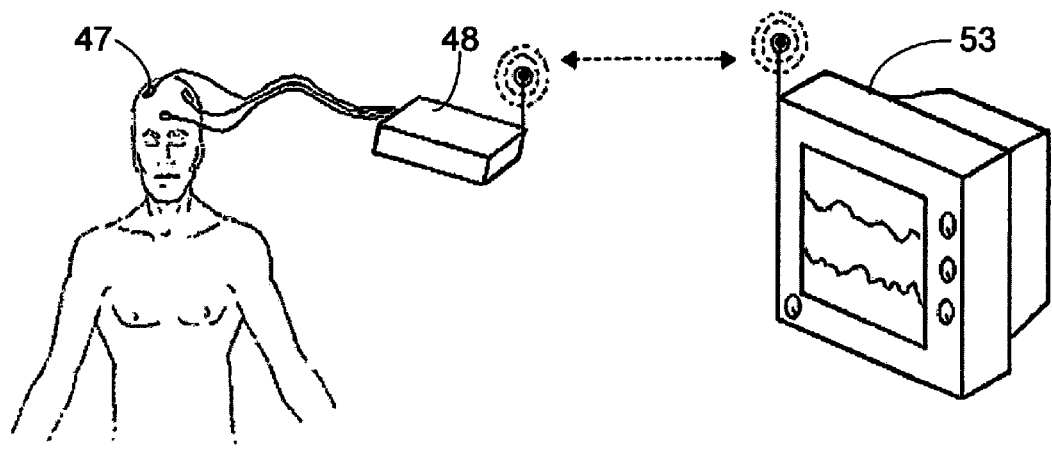
FIG. 17 illustrates a schematic of an EEG monitoring system in accordance with certain embodiments

FIG. 17 shows the schematic of an EEG monitoring system according to certain embodiments. Signals recorded by the electrodes 47, placed on the scalp of a subject, are transmitted to the acquisition module 48, which in turn transmits the signal via a wireless link to a computer 53. The computer 53 contains the processing module 49 embedded with the code 50, the storage module 51 and the display module 52, as previously described in FIG. 16. The computer 53 may display the quantitative index data in a manner similar to one of the graphs illustrated in FIG. 5, for example. The connection between the electrodes 47, the acquisition module 48, and the computer 53 can be via wired or wireless connectors, or other means of communication. A wireless design allows the acquisition module and the computer to be placed at a distance, allowing free movement of healthcare professionals in the immediate vicinity of the patient. Data acquisition is accomplished by the acquisition module, which may in certain embodiments allow for connection of a plurality of differential input channels and a reference connection. The acquisition module may be configured for compact size, wireless communication, battery power, and electrical signal isolation in certain embodiments.

Figure 18:
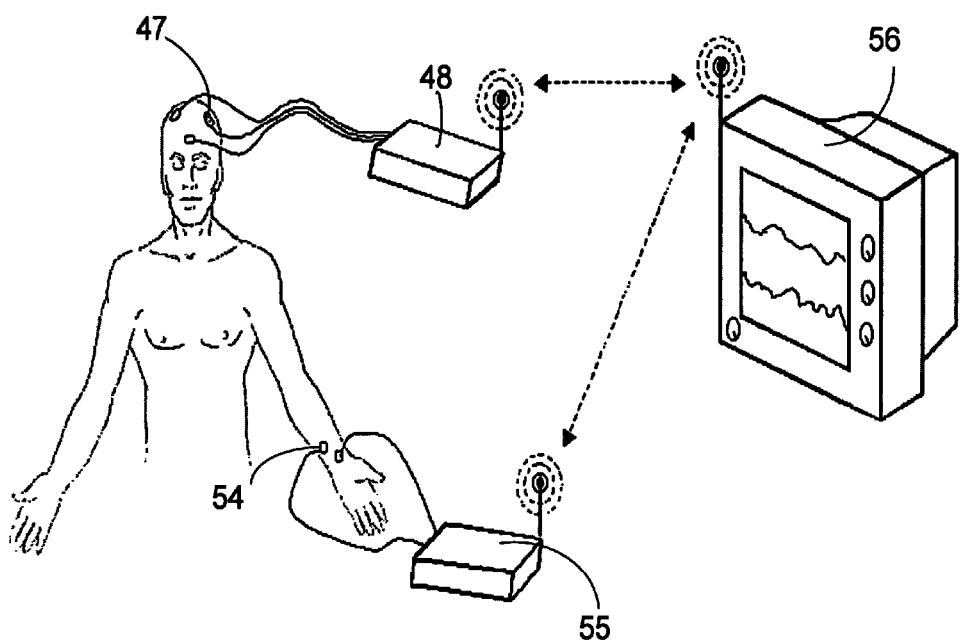
FIG. 18 illustrates a schematic of an EP monitoring system in accordance with certain embodiments.

FIG. 18 illustrates an EP monitoring system according to certain embodiments. An computer 56 directs a stimulation module 55 to deliver a stimulus to a subject via stimulation electrodes 54. The recording electrodes 47 then record the subject's EP responses and transmits them to the acquisition module 48. The acquisition module 48 then transmits the signal to the computer 56. The EP computer 56 may contain the processing module 49 embedded with the code 50, the storage module 51, and the display module 52. The connection between the computer 56, the simulation module 55, and the stimulation electrode 54 may be via wired or wireless connectors or other means of communication. Similarly, the connection between the electrodes 47, the acquisition module 48, and the computer 56 may be wired, wireless, or through other means of communication.

Figure 19:
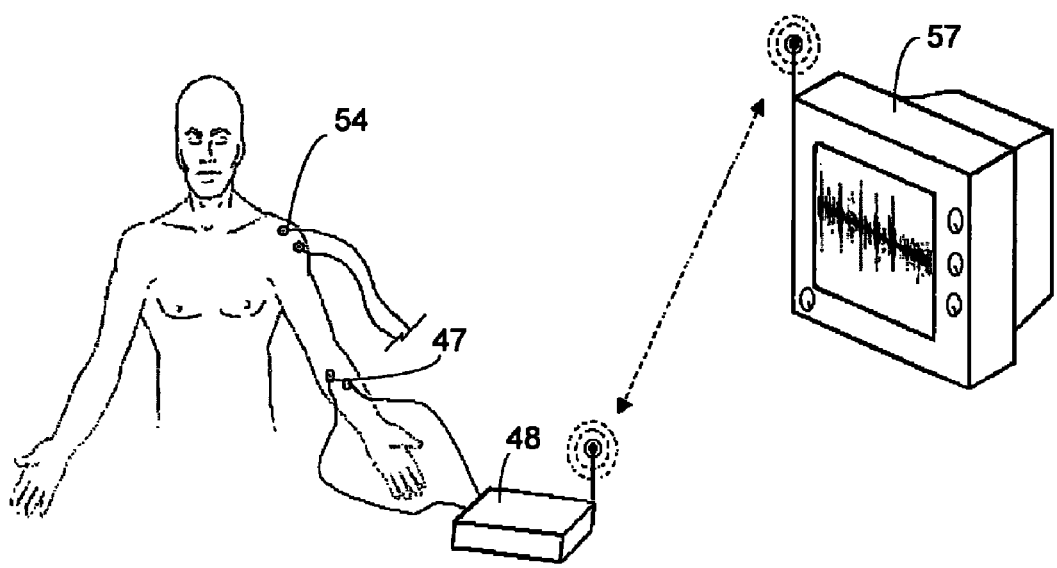
FIG. 19 illustrates a schematic of an EMG monitoring system in accordance with certain embodiments.

FIG. 19 demonstrates the schematic of an EMG monitoring system according to certain embodiments. Stimulation electrodes 54 deliver a stimulus to a subject. The EMG signals recorded by electrodes 47 are transmitted to the acquisition module 48 via wires, wireless link, or other means of communication. The acquisition module 48 then transmits the signals to a computer 57, which may contain the processing module 49 embedded with the code 50, the storage module 51, and the displaying module 52 previously described in FIG. 16. The connection between the computer 57 and the acquisition module 48 may also be via wires, wireless link, or other means of communication.

Figure 20:
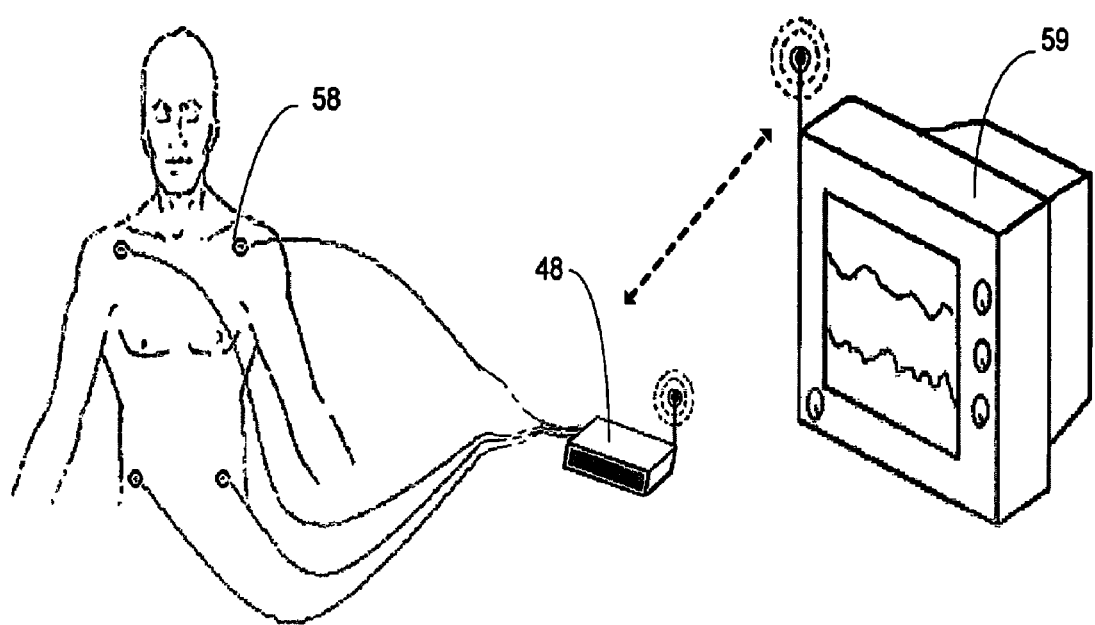
FIG. 20 illustrates a schematic of an EKG monitoring system in accordance with certain embodiments.

FIG. 20 describes an EKG monitoring system according to certain embodiments. Cardiac electrodes 58 may be located inside the heart or outside the heart. Thus, cardiac electrodes may include both body surface electrodes and intra-cardiac electrodes. The cardiac electrodes 58 record signals and transmit them to the acquisition module 48, which in turn communicates with an computer 59. The computer 59 contains the processing module 49 embedded with the code 50, the storage module 51, and the display module 52, as previously described in FIG. 16. The connection between the cardiac electrodes 58, the acquisition module 48, and the computer 59 may be via wires, wireless link, or other means of communication.

Figure 21:
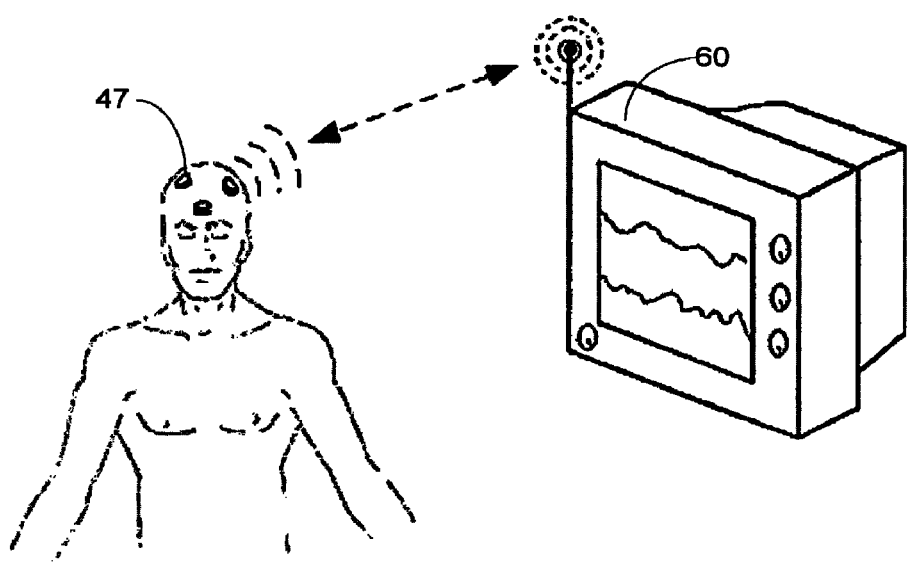
FIG. 21 illustrates a schematic of a single unit monitoring system in accordance with certain embodiments.

FIG. 21 illustrates the schematic of a single unit monitoring system according to certain embodiments. Electrodes 47 record bioelectrical signals and transmit them to a computer 60. The computer 60 may incorporate the acquisition module 48, the processing module 49 with the embedded code 50, the storage module 51, and the display module 52 into one single unit. The communication between the electrodes 47 and the computer 60 may be via wires, wireless link, or other means of communication. This system can be configured to record EEG, EP, EMG, and EKG according to certain embodiments.

FIG. 22 shows the schematic of a system with a computer under brain control in the manner of brain-computer-interface. Electrodes 47 record bioelectrical signals from the brain and transmit them to the acquisition module 48, which in turn transmits the signals to a computer 61 containing the processing module 49 with the embedded code 50. Upon computation of the quantitative index, the computer 61 transmits the quantitative index to a computer under brain control 62. The computer under brain control 62 may then perform an action directly. Alternatively, the computer under brain control 62 may perform an action through a device 71 according to certain embodiments. Examples of the device 71 may include but are not limited to prosthetics, instruments, and machines. For example, the device 71 may be a prosthetic arm which may perform a task such as physically moving a pen. The communication between the electrodes 47, the acquisition module 48, the computer 61 containing processing module 49, the computer under brain control 62, and the device 71 can be via wires, wireless link, or other means of communication. In certain embodiments, some or all of the electrodes 47, acquisition module 48, the computer 61, the computer under brain control 62, and the device 71 may be incorporated into a single unit.

Figure 23:
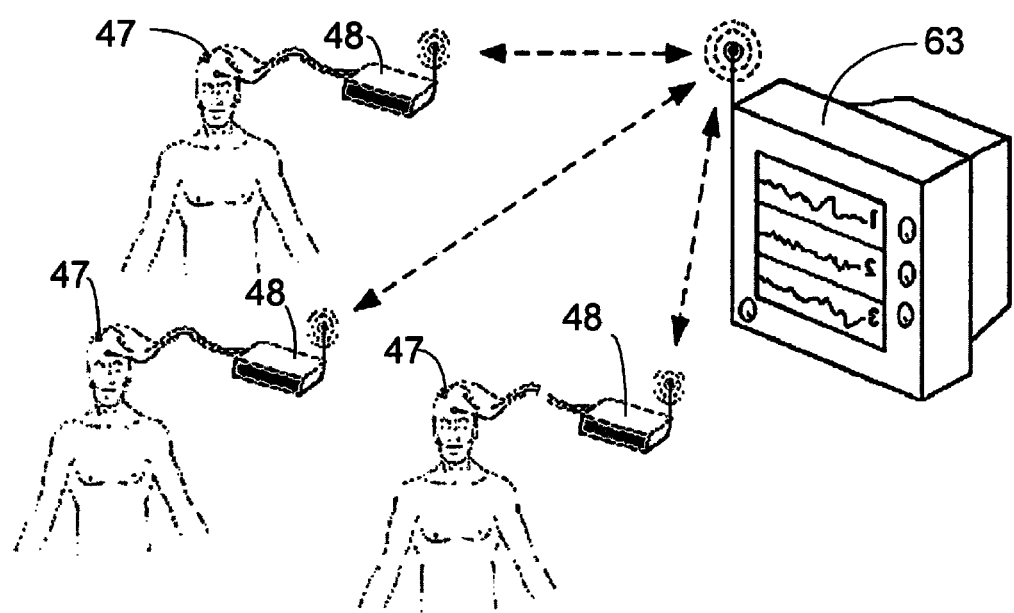
FIG. 23 illustrates a central monitoring system in accordance with certain embodiments.

FIG. 23 depicts a central monitoring system according to certain embodiments. One set of electrodes 47 records signals from one subject, and transmit the signal to one acquisition module 48. Multiple acquisition modules 48 then transmit the signals to one single central computer 63. The central computer 63 contains the processing module 49 imbedded with the code 50, the storage module 51, and the display module 52. Quantitative index data from multiple subjects are then simultaneously displayed on one screen. The connection between the electrodes 47, the acquisition modules 48, and the central computer 63 may be via wires, wireless link, or other means of communication.

Figure 24:
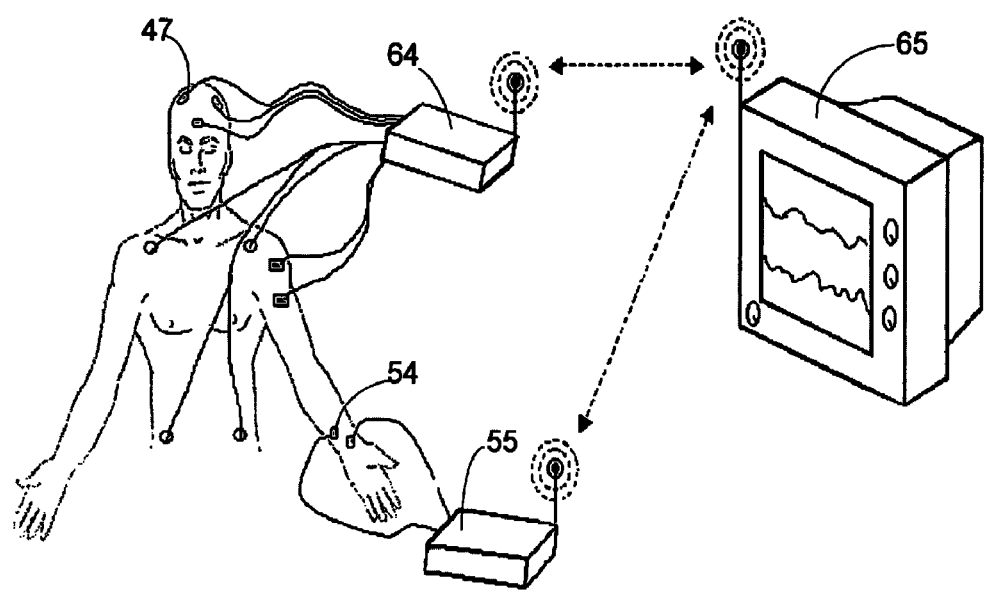
FIG. 24 illustrates a multi-modal monitoring system in accordance with certain embodiments.

In certain embodiments, multiple classes of bioelectrical signal can be used together to generate one single comprehensive quantitative index. In one embodiment simultaneous recording of EEG signals and EP signals can be used to monitor the overall neurological status of a comatose patient after cardiac arrest. In another embodiment, EP and EMG may be recorded concurrently to generate one single comprehensive quantitative index which reflects the overall status of neuromuscular system. In yet another embodiment, EP, EEG, and EMG can be simultaneously recorded to yield a comprehensive quantitative index which reflects the overall status of the entire neurological and neuromuscular system. In one further embodiment shown in FIG. 24, EEG, EP, EMG, and EKG are simultaneously collected by a single monitoring system. In FIG. 24, a multi-modal monitor 65 instructs the stimulation module 55 to give a stimulus through the stimulation electrodes 54. A multi-modal acquisition module 64 then simultaneously collects EKG, EEG, EMG, and EP. The signals are then transmitted to the multi-modal monitor 65 containing the processing module 49 imbedded with the code 50, the storage module 51, and the display module 52. The processing module containing the code 50 constructs a quantitative index reflecting the overall status of the subject, taking both the cardiac and neurological systems into consideration. The quantitative index is then displayed by the display module 52.

It will, of course, be understood that modifications of the present invention, in its various aspects, will be apparent to those skilled in the art. Additional embodiments are possible, their specific parameters depending upon the particular application.

What is claimed is:

1. A method for determining a condition of a subject, comprising:
   obtaining a signal, the signal including a plurality of determinable parameters;
   determining, by a computer, at least two of the plurality of determinable parameters from the signal to yield determined parameters; and
   applying a weighting factor, by a computer, to each of the determined parameters to yield weighted parameters, and combining the weighted parameters, by a computer, to determine a numeric value relating to the condition of the subject;
   wherein the condition of the subject is a neurological condition, wherein the neurological condition comprises a neuronal injury, and wherein the neuronal injury occurs after cardiac arrest.

2. A method according to claim 1, further comprising segmenting the signal into a plurality of windows of a preset time.

3. A method according to claim 2, further comprising evaluating the plurality of windows of the signal for artifacts using a threshold-based artifact detection method, and discarding a window when the signal in that window exceeds a predetermined threshold value.

4. A method according to claim 3, further comprising, after evaluating the plurality of windows of the signal, filtering the remaining windows of the signal.

5. A method according to claim 1, wherein the plurality of determinable parameters includes at least two parameters selected from the group consisting of temporal, spectral, and probabilistic.

6. A method according claim 1, wherein the plurality of determinable parameters include at least two parameters selected from the group consisting of amplitude, latency, frequency, entropy, power, and energy.

7. A method according to claim 1, wherein the numerical value relating to the condition of the subject is used to determine treatment options including at least one of modality of treatment, magnitude of treatment, dosage of treatment, and timing of treatment.

8. A method according to claim 1, wherein the numeric value relating to the condition of the subject is used to monitor response to treatments.

9. A method according to claim 1, wherein the numerical value is used to perform at least one operation selected from the group consisting of: (i) predicting neurological outcome for patients in coma after cardiac arrest; and (ii) monitoring response to hypothermia treatment.

10. A method according to claim 1, wherein the neuronal injury is caused by at least one condition selected from the group consisting of: (i) lack of oxygen; and (ii) lack of blood flow.

11. A method according to claim 1, wherein the signal comprises at least one signal selected from the group consisting of: (i) an electroencephalogram (EEG) signal; (ii) an evoked potential (EP) signal; (iii) an electromyogram (EMG) signal; and (iv) an electrocardiogram (EKG) signal.

12. A method according to claim 11, wherein the signal is at least one signal selected from the group consisting of a single channel signal and a multiple channel signal.

13. A method according to claim 11, wherein the plurality of determinable parameters include parameters selected from the group consisting of temporal, spectral, and probabilistic parameters.

14. A method according to claim 11, wherein the plurality of determinable parameters includes a plurality of parameters selected from the group consisting of amplitude, frequency, power, and entropy.

15. A method according to claim 11, wherein the signal includes an EKG signal, and the EKG signal is obtained using at least one electrode selected from the group consisting of an intra-cardiac electrode and a surface electrode.

16. A method according to claim 15, wherein the plurality of determinable parameters include a plurality of parameters selected from the group consisting of duration, RR interval, heart rate variability, amplitude, energy, power, frequency entropy, and offset.

17. A method for determining a condition of a subject, comprising:
 obtaining a signal, the signal including a plurality of determinable parameters;
 determining, by a computer, at least two of the plurality of determinable parameters from the signal to yield determined parameters; and
 applying a weighting factor, by a computer, to each of the determined parameters to yield weighted parameters, and combining the weighted parameters, by a computer, to determine a numeric value relating to the condition of the subject;
 wherein the condition of the subject is a neurological condition;
 wherein the neurological condition comprises a neuronal injury caused by antenatal hypoxia of a fetus, and wherein the antenatal hypoxia occurs during labor.

18. A method for determining a condition of a subject, comprising:
 obtaining a signal, the signal including a plurality of determinable parameters;
 determining, by a computer, at least two of the plurality of determinable parameters from the signal to yield determined parameters; and
 applying a weighting factor, by a computer, to each of the determined parameters to yield weighted parameters, and combining the weighted parameters, by a computer, to determine a numeric value relating to the condition of the subject;
 wherein the signal comprises an EEG signal, and the EEG signal includes information relating to a seizure.

19. A method for determining a condition of a subject, comprising:
 obtaining a signal, the signal including a plurality of determinable parameters;
 determining, by a computer, at least two of the plurality of determinable parameters from the signal to yield determined parameters; and
 applying a weighting factor, by a computer, to each of the determined parameters to yield weighted parameters, and combining the weighted parameters, by a computer, to determine a numeric value relating to the condition of the subject;
 wherein the signal comprises an evoked potential (EP) signal, and the plurality of determinable parameters includes a plurality of parameters selected from the group consisting of amplitude, latency, central conduction time, correlation of amplitude and latency, frequency, power, and entropy.

20. A method according to claim 19, wherein a peak selected for analysis of the determinable parameters includes at least one peak selected from the group consisting of N13, N20, P25, and N35.

21. A method for determining a condition of a subject, comprising:
 obtaining a signal, the signal including a plurality of determinable parameters;
 determining, by a computer, at least two of the plurality of determinable parameters from the signal to yield determined parameters; and
 applying a weighting factor, by a computer, to each of the determined parameters to yield weighted parameters, and combining the weighted parameters, by a computer, to determine a numeric value relating to the condition of the subject;
 wherein the signal comprises an EEG signal, and the EEG signal includes information relating to neuronal injury.

22. A method according to claim 21,
 wherein the plurality of determinable parameters includes a plurality of parameters selected from the group consisting of amplitude, frequency, power, and entropy; and
 wherein the entropy includes a comparison of the entropy of the EEG signal in selected frequency bands.

23. A method according to claim 21,
 wherein the plurality of determinable parameters includes a plurality of parameters selected from the group consisting of amplitude, frequency, power, and entropy; and
 wherein the amplitude includes at least one amplitude selected from the group consisting of mean amplitude, instantaneous amplitude, and normalized amplitude.

24. A method according to claim 21,
 wherein the plurality of determinable parameters includes a plurality of parameters selected from the group consisting of amplitude, frequency, power, and entropy; and
 wherein the frequency includes at least one of (i) a distribution of frequencies; (ii) a mean frequency; and (iii) a spectral edge frequency.

25. A method according to claim 20,
 wherein the plurality of determinable parameters includes a plurality of parameters selected from the group consisting of amplitude, frequency, power, and entropy; and
 wherein the frequency includes a spectral edge frequency, wherein the spectral edge frequency is a 95% spectral edge frequency.

26. A method according to claim 20,
 wherein the plurality of determinable parameters includes a plurality of parameters selected from the group consisting of amplitude, frequency, power, and entropy; and
 wherein the power includes a power distribution in a plurality of frequency bands.

27. A method according to claim 26, wherein the plurality of frequency bands includes at least three dominant frequency bands.

28. A method for determining a condition of a subject, comprising:
 obtaining a signal including a plurality of determinable parameters;
 determining at least two of the plurality of determinable parameters to yield determined parameters;
 applying an algorithm, by a computer, that assigns a weighting factor to each of the determined parameters to yield weighted parameters, and combining the weighted parameters, by a computer, to yield a numeric value relating to the condition of the subject; and
 training the algorithm by inputting a plurality of sample signals, each sample signal having a corresponding predetermined value, wherein the algorithm, by a computer, adjusts the weighting factors so that the combining the weighted parameters for each sample signal yields the corresponding predetermined value.

29. A method according to claim 28, further comprising determining a clinical factor and adjusting the algorithm based on the clinical factor.

30. A method according to claim 29, wherein the clinical factor comprises at least one factor selected from the group consisting of: (i) a clinician impression factor; (ii) a risk level of individual subject factor; (iii) a clinical scoring system factor; (iv) a vital sign factor based on one or more vital signs vital signs; (v) an oxygen saturation factor; (vi) a laboratory test result factor based on one or more laboratory test results from at least one of bodily fluids and tissues; and (vii) a factor based on the subject's ability to communicate his intent to the computer under brain control.

31. A method according to claim 30, wherein the clinical scoring system includes at least one system selected from the group consisting of: (i) Glascow Coma scale (GCS); (ii) Apgar score; (iii) Cerebral Performance Category (CPC); (iv) coronary artery disease assessment score; (v) Fugl-Meyer assessment (FMA); (vi) modified Ashworh scale (MAS); and (vii) manual muscle test (MMT) scores.

32. A method according to claim 30, wherein the vital signs include at least one vital sign selected from the group consisting of: (i) blood pressure; (ii) temperature; (iii) heart rate; (iv) respiratory rate; (v) intracranial pressure (ICP); (vi) pulmonary wedge pressure; and (vii) central venous pressure.

33. A method according to claim 30, wherein the laboratory test results from bodily fluids and tissues includes at least one test result from the group consisting of: (i) anti-seizure medication level; (ii) creatine kinase-BB isoenzyme level; (iii) neurone-specific enolase level; (iv) astroglial protein S-100 level; (v) creatine kinase-MB level; (vi) troponin level; and (vii) myoglobin level.

34. A method according to claim 29, wherein the clinical factor comprises the subject's ability to communicate his intent to the computer under brain control.

35. A method according to claim 28, wherein the plurality of sample signals includes at least one signal selected from the group consisting of: (i) EEG; (ii) EMG; (iii) evoked potential (EP); and (iv) EKG.

* * * * *